United States Patent [19]

Pease et al.

[11] Patent Number: 5,618,732
[45] Date of Patent: Apr. 8, 1997

[54] METHOD OF CALIBRATION WITH PHOTOACTIVATABLE CHEMILUMINESCENT MATRICES

[75] Inventors: John S. Pease, Los Altos; Hrair Kirakossian, San Jose; Daniel B. Wagner, Sunnyvale; Edwin F. Ullman, Atherton, all of Calif.

[73] Assignee: Behringwerke AG, Marburg, Germany

[21] Appl. No.: 434,617

[22] Filed: May 4, 1995

Related U.S. Application Data

[62] Division of Ser. No. 923,069, Jul. 31, 1992.

[51] Int. Cl.$^6$ .......................... G01N 21/64; G01N 21/76
[52] U.S. Cl. ..................... 436/8; 436/172; 436/905
[58] Field of Search .................................. 436/8, 172, 905

[56] References Cited

U.S. PATENT DOCUMENTS

| | | | |
|---|---|---|---|
| 3,850,578 | 11/1974 | McConnell | 23/230 B |
| 3,996,345 | 12/1976 | Ullman et al. | 424/12 |
| 4,174,384 | 11/1979 | Ullman et al. | 424/8 |
| 4,193,983 | 3/1980 | Ullman et al. | 424/12 |
| 4,199,559 | 4/1980 | Ullman et al. | 424/8 |
| 4,220,450 | 9/1980 | Maggio | 23/230 B |
| 4,226,993 | 10/1980 | Bucker et al. | 544/237 |
| 4,233,402 | 11/1980 | Maggio et al. | 435/7 |
| 4,261,968 | 4/1981 | Ullman et al. | 424/8 |
| 4,277,437 | 7/1981 | Maggio | 422/61 |
| 4,299,916 | 11/1981 | Litman et al. | 435/6 |
| 4,311,712 | 1/1982 | Evans et al. | 424/365 |
| 4,315,998 | 2/1982 | Neckers et al. | 525/332 |
| 4,318,707 | 3/1982 | Litman et al. | 23/230 B |
| 4,380,580 | 4/1983 | Boguslaski et al. | 435/7 |
| 4,383,031 | 5/1983 | Boguslaski et al. | 435/7 |
| 4,483,921 | 11/1984 | Cole | 435/7 |
| 4,483,929 | 11/1984 | Szoka | 436/533 |
| 4,485,054 | 11/1984 | Mezei et al. | 264/4.6 |
| 4,522,803 | 6/1985 | Lenk et al. | 424/1.1 |
| 4,529,561 | 7/1985 | Hunt et al. | 264/4.3 |
| 4,576,912 | 3/1986 | Yaverbaum et al. | 435/7 |
| 4,588,578 | 5/1986 | Fountain et al. | 424/1.1 |
| 4,650,770 | 3/1987 | Liu et al. | 436/523 |
| 4,652,533 | 3/1987 | Jolley | 436/518 |
| 4,654,300 | 3/1987 | Zuk et al. | 435/7 |
| 4,857,652 | 8/1989 | Schaap | 549/510 |
| 4,891,324 | 1/1990 | Pease et al. | 436/519 |
| 4,931,223 | 6/1990 | Bronstein et al. | 252/700 |
| 4,950,588 | 8/1990 | Dattagupta | |
| 4,956,477 | 9/1990 | Bronstein et al. | 549/221 |
| 4,959,182 | 9/1990 | Schaap | 252/700 |
| 4,962,192 | 10/1990 | Schaap | 536/18.1 |
| 4,978,614 | 12/1990 | Bronstein | 435/21 |
| 5,017,473 | 5/1991 | Wagner | 435/7.92 |
| 5,094,958 | 3/1992 | Klainer et al. | 436/172 |
| 5,272,090 | 12/1993 | Gavish et al. | 436/172 X |

FOREIGN PATENT DOCUMENTS

| | | |
|---|---|---|
| 0070685A2 | 1/1983 | European Pat. Off. . |
| 0070687A2 | 1/1983 | European Pat. Off. . |
| 0144914A2 | 6/1985 | European Pat. Off. . |
| 0229943A2 | 7/1987 | European Pat. Off. . |
| 0232967A2 | 8/1987 | European Pat. Off. . |
| 0315364A2 | 5/1989 | European Pat. Off. . |
| 0324202A1 | 7/1989 | European Pat. Off. . |
| 0322926A2 | 7/1989 | European Pat. Off. . |
| 0345776A2 | 12/1989 | European Pat. Off. . |
| 0352713A1 | 1/1990 | European Pat. Off. . |
| 0401001A2 | 12/1990 | European Pat. Off. . |
| 0421788A2 | 4/1991 | European Pat. Off. . |
| 0515194A | 11/1992 | European Pat. Off. . |
| WO88/00695 | 1/1988 | WIPO . |
| WO89/06226 | 7/1989 | WIPO . |
| WO90/00164 | 1/1990 | WIPO . |
| WO90/02742 | 3/1990 | WIPO . |
| WO90/07511 | 7/1990 | WIPO . |

OTHER PUBLICATIONS

Oser, et al., Angew. Chem. Int. Ed. Engl., (1990), vol. 29:10, pp. 1167–1169 "Nonradioactive Assay of DNA Hybridization by DNA–Template–Mediated Formation of a Ternary Tb$^{III}$ Complex in Pure Liquid Phase".

Heller, et al., Rapid Detection and Identification of Infectious Agents, (1985) Academic Press, Inc., pp. 245–257 "Chemiluminescent and Fluorescent Probes for DNA Hybridization Systems".

Hara, et al., Bull. Chem. Soc. Jpn., (Oct. 1984), vol. 57: pp. 3009–3010 "Immunoassay Using a Metal–complex Compound as a Chemiluminescent Catalyst. IV. The Investigation of a Metal Porphine Complex as a Labeling Reagent".

Kuschnir, et al., Chemical Communications, (1969), vol. 193 p. 193 "Photosensitized Chemiluminescence of Luminol, 6–Aminophthalazine–1,4(2H,3H)–dione".

Cardullo, et al., Proc. Natl. Acad. Sci. U.S.A., (Dec. 1988), vol. 85: pp. 8790–8794 "Detection of nucleic acid hybridization by nonradiative fluorescence resonance energy transfer".

(List continued on next page.)

*Primary Examiner*—Jeffrey Snay
*Attorney, Agent, or Firm*—Theodore J. Leitereg

[57] ABSTRACT

Methods for labeling a material are disclosed. The methods comprise combining with the material (a) a photosensitizer capable upon irradiation of generating singlet oxygen and (b) a chemiluminescent compound capable of being activated by singlet oxygen wherein the photosensitizer and the chemiluminescent compound are incorporated in a particulate matrix or a non-particulate solid matrix. The particulate matrix can be solid or fluid. The methods allow for generating delayed luminescence, which can be realized upon irradiation of the matrix. The methods have application to the determination of an analyte in a medium suspected of containing the analyte. One method comprises subjecting a medium suspected of containing an analyte to conditions under which a complex of specific binding pair (sbp) members is formed in relation to the presence of the analyte and determining whether the sbp member complex has formed by employing as a label a single composition having both chemiluminescent and photosensitizer properties. Upon activation of the photosensitizer property singlet oxygen is generated and activates the chemiluminescent property. Compositions and kits are also disclosed.

3 Claims, No Drawings

OTHER PUBLICATIONS

Morrison, et al., Analytical Biochemistry, (1989), vol. 183: pp. 231–244 "Solution–Phase Dection of Polynucleotide Using Interacting Fluorescent Labels and Competitive Hybridization".

Zomer, et al., Analytica Chemica Acta, (1989), vol. 227: pp. 11–19 "Chemiluminogenic Labels, Old and New".

Morrison, Analytical Biochemistry, (1988), vol. 174, pp. 101–120 "Time–Resolved Detection of Energy Transfer: Theory and Application to Immunoassays".

O'Connell, et al., Clinical Chemistry, (1985), vol. 31:9, pp. 1424–1426 "A Highly Sensitive Immunoassay System Involving antibody–Coated Tubes and Liposome–Entrapped Dye".

Yemul, et al., Proc. Natl. Acad. Sci. U.S.A., (Jan. 1987) 1987, vol. 84, pp. 246–250 "Selective killing of t lymphocytes by phototoxic liposomes".

Mew, et al., Journal of Immunology, (1983), vol. 130:3, pp. 1473–1477 "Photoimmunotherapy: Treatment of animal tumors with tumor–specific monoclonal antibody–hematoporphyrin conjugates".

Hirschfeld, Applied Optics, (1976), vol. 15:12, pp. 3135–3139 "Oqantum efficiency independence of the time integrated emission from afluorescent molecule".

Turro, et al., Journal of the American Chemical Society, vol. 100:22 (Oct. 25, 1978) pp. 7110–7112, "Generation, Diffusivity, and Reactivity of Singlet Oxygen in Polymer Matrices. A Convenient and Sensitive Chemiluminescent Technique".

METHOD OF CALIBRATION WITH PHOTOACTIVATABLE CHEMILUMINESCENT MATRICES

This is a divisional of application Ser. No. 07/923,069, filed Jul. 31, 1992.

BACKGROUND OF THE INVENTION

1. Field of the Invention

This invention relates to photoactivatable chemiluminescent matrices and to methods, compositions and kits for determining an analyte in a sample.

The clinical diagnostic field has seen a broad expansion in recent years, both as to the variety of materials (analytes) that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting low concentrations of these materials is enhanced by the relatively small sample sizes that can be utilized.

In developing an assay there are many considerations. One consideration is the signal response to changes in the concentration of analyte. A second consideration is the ease with which the protocol for the assay may be carried out. A third consideration is the variation in interference from sample to sample. Ease of preparation and purification of the reagents, availability of equipment, ease of automation and interaction with material of interest are some of the additional considerations in developing a useful assay.

One broad category of techniques involves the use of a receptor which can specifically bind to a particular spacial and polar organization of a labeled ligand as a function of the presence of the analyte. The observed effect of binding by the receptor will depend upon the label. In some instances the binding of the receptor merely provides for a differentiation in molecular weight between bound and unbound labeled ligand. In other instances the binding of the receptor will facilitate separation of bound labeled ligand from free labeled ligand or it may affect the nature of the signal obtained from the label so that the signal varies with the amount of receptor bound to labeled ligand. A further variation is that the receptor is labeled and the ligand unlabeled. Alternatively, both the receptor and ligand are labeled or different receptors are labeled with different labels where the labels interact when in close proximity and the amount of ligand present affects the degree to which the labels of the receptor may interact.

There is a continuing need for new and accurate techniques that can be adapted for a wide spectrum of different ligands or be used in specific cases where other methods may not be readily adaptable.

Homogeneous immunoassays have previously been described for small molecules. These assays include SYVA's FRAT® assay, EMIT® assay, enzyme channeling immunoassay, and fluorescence energy transfer immunoassay (FETI); enzyme inhibitor immunoassays (Hoffman LaRoche and Abbott Laboratories): fluorescence polarization immunoassay (Dandlicker), among others. All of these methods have limited sensitivity, and only a few including FETI and enzyme channeling, are suitable for large multi-epitopic analytes.

Luminescent compounds, such as fluorescent compounds and chemiluminescent compounds, find wide application in the assay field because of their ability to emit light. For this reason, luminescers have been utilized as labels in assays such as nucleic acid assays and immunoassays. For example, a member of a specific binding pair is conjugated to a luminescer and various protocols are employed. The luminescer conjugate can be partitioned between a solid phase and a liquid phase in relation to the amount of analyte in a sample suspected of containing the analyte. By measuring the luminescence of either of the phases, one can relate the level of luminescence observed to a concentration of the analyte in the sample.

Particles, such as liposomes and erythrocyte ghosts, have been utilized as carriers of encapsulated water soluble materials. For example, liposomes have been employed to encapsulate biologically active material for a variety of uses, such as drug delivery systems wherein a medicament is entrapped during liposome preparation and then administered to the patient to be treated.

Particles, such as latex beads and liposomes, have also been utilized in assays. For example, in homogeneous assays an enzyme may be entrapped in the aqueous phase of a liposome labelled with an antibody or antigen. The liposomes are caused to release the enzyme in the presence of a sample and complement. Antibody or antigen-labeled liposomes, having water soluble fluorescent or non-fluorescent dyes encapsulated within an aqueous phase vesicle or lipid soluble dyes dissolved in the lipid bilayer of a lipid, have also been utilized to assay for analytes capable of entering into an immunochemical reaction with the surface bound antibody or antigen. Detergents have been used to release the dyes from the aqueous phase of the liposomes.

Chemiluminescent labels offer exceptional sensitivity in ligand binding assays, but one or more chemical activation steps are usually needed. Fluorescent labels do not have this deficiency but are less sensitive.

Chemiluminescent labels have been described for immunoassays and nucleic acid assays where a group, which is covalently bound to a binding partner, on chemical activation emits light. A nucleic and assay kit utilizing an acridinium ester is sold by Genprobe Pace2 system®, San Diego, Calif.) and MagicLite® immunoassay kits using this type of label are sold by CIBA-GEIGY (Basel, Switzerland). Energy transfer from a labeled nucleic acid probe to a fluorescent acceptor bound to a second probe has been described by Heller, et al., I and II, infra, for a sandwich nucleic acid assay. Maggio I, infra, discusses a similar procedure for immunoassays. Transfer of energy from a luminescer covalently bound to a polynucleotide to an intercalated fluorophore was mentioned by Heller, et al., IV, infra. Transfer from an intercalated dye to a fluorescer on a polynucleotide was described recently by Cardullo, et al., infra. Further McCapra, infra, has described the use of photosensitizers as labels where the photosensitizer activates oxygen to its singlet state, which in turn reacts with a compound that on heating produces light.

2. Brief Description of the Related Art

European Patent Application 0 421 788 A2 discloses a haloperoxidase-acid-oxidant chemilumescence assay system for determining the presence or amount of an analyte in a liquid sample. The system utilizes haloperoxidase, halide, oxidant and chemiluminigenic substrate. The indicator system acts as a synthesizer of highly reactive singlet molecular oxygen, which reacts with the chemiluminigenic substrate to yield an excited state, oxidized reaction product. The excited state reaction product then relaxes to a lower energy state with the emission of measurable light in an amount related to the amount of each of the reaction participants. The chemiluminigenic substrate may be used as a label and may be coupled to a ligand such as a protein, hormone, hapten, steroid, lectin, nucleic acid, metabolite, antigen, antibody, nucleic acid probe, bacteriophage or virus (page 10, lines 8–17).

Oser, et al., *Angew. Chem. Int. Ed. Engl.*, 29:1167–1169 (1990) describes a nonradioactive assay of DNA hybridization by DNA-template-mediated formation of a ternary Tb(III) complex in pure liquid phase.

U.S. Pat. No. 5,017,473 discloses a homogeneous chemiluminescence immunoassay using a light absorbing material.

European Patent Application No. 0,345,776 (McCapra) discloses specific binding assays that utilize a sensitizer as a label. The sensitizers include any moiety which, when stimulated by excitation with radiation of one or more wavelengths or other chemical or physical stimulus (e.g., electron transfer, electrolysis, electroluminescence or energy transfer) will achieve an excited state which (a) upon interaction with molecular oxygen will produce singlet molecular oxygen, or (b) upon interaction with a leuco dye will assume a reduced form that can be returned to its original unexcited state by interaction with molecular oxygen resulting in the production of hydrogen peroxide. Either interaction with the excited sensitizer will, with the addition of reagents, produce a detectible signal.

European Patent Application No. 0,070,685 (Heller, et al. I) describes a homogeneous nucleic acid hybridization diagnostic by non-radiative energy transfer.

A light-emitting polynucleotide hybridization diagnostic method is described in European Patent Application No. 0,070,687 (Heller, et al. II).

European Patent Application No. 0,232,967 (Morrison I) discusses methods and compositions for performing assays for target polynucleotide strands. The methods include contacting a sample with a reagent that includes a first and a second polynucleotide probe. The first and second probes are capable of assuming a first position wherein the probes are bound to each other and a second position wherein the probes are bound to a target. The probes include label moieties capable of interacting to produce a signal indicative of the probes being in one of the two positioned.

European Patent Application No. 0,315,364 describes an immunochemical assay to determine the presence or concentration of antigen or antibodies in a fluid. The assay comprises (a) forming a ternary complex of a first labeled antibody or antigen, a second labeled antibody or antigen, and the antigen or antibody to be determined, and (b) detecting a signal produced in the presence of at least one substrate, by an interaction between the first label and the second label, enhanced by their proximity to each other bound to the antigenic substance.

European Patent Application No. 0,229,943 (Heller, et al. III) describes fluorescent Stokes shift probes for a polynucleotide hybridization assays.

U.S. Pat. No. 4,226,993 (Buckler, et al.) describes immuno-functionalized phthalhydrazides, which are useful as intermediates in the synthesis of chemiluminescent phthalhydrazide-labeled conjugates. The conjugates are useful as reagents in specific binding assays for determining ligands or their specific binding partners in liquid media.

U.S. Pat. Nos. 4,380,580 and 4,383,031 (Boguslaski, et al. I and Boguslaski, et al. II) respectively describe heterogeneous and homogeneous chemiluminescent specific binding assays.

U.S. Pat. No. 4,220,450 (Maggio I) discusses chemically induced fluorescence immunoassays.

U.S. Pat. No. 4,652,533 (Jolley) describes a method of solid phase immunoassay incorporating a luminescent label.

U.S. Pat. No. 4,277,437 (Maggio II) discloses kits for carrying out chemically induced fluorescence immunoassays.

Heller, et al. (IV), describe chemiluminescent and fluorescent probes for DNA hybridization systems in "Rapid Detection and Identification of Infectious Agents" (1985) Academic Press, Inc., pages 245–257.

Hara, et al., describe an immunoassay using a metal-complex compound as a chemiluminescent catalyst in *Bull. Chem. Soc. Jpn.* (1984) 57:3009–3010.

Kuschnir, et al., describe photosensitized chemiluminescence of luminol in 6-aminophthalazine-1,4-(2H3H)-dione in *Chemical Communications* (1969) 193.

The detection of nucleic acid hybridization by non-radiative fluorescence residence energy transfer is described by Cardullo, et al., in *Proc. Natl. Acad. Sci. U.S.A.* (1988) 85:8790–8794.

Morrison, et al. describe a solution-phase detection of polynucleotides using interactive fluorescent labels and competitive hybridization in *Analytical Biochemistry* (1989) 189:231–244.

Zomer, et al. describe chemiluminogenic labels in *Analytica Chemica Acta* (1989) 227:11–19.

Morrison II discusses time-resolved detection of energy transfer: theory and application to immunoassays in *Analytical Biochemistry* (1988) 174:101–120.

U.S. Pat. No. 4,299,916 (Litman, et al. I) describes preferential signal production on a surface in immunoassays.

U.S. Pat. No. 4,233,402 (Maggio, et al.) describes reagents and methods employing channeling.

U.S. Pat. No. 4,261,968 (Ullman, et al. I) describes fluorescence quenching with immunological pairs in immunoassays.

U.S. Pat. No. 4,318,707 (Litman, et al. II) discusses a macromolecular fluorescent quencher particle in specific receptor assays.

U.S. Pat. No. 4,650,770 (Liu, et al.) discusses energy absorbing particle quenching in light-emitting competitive protein binding assays.

U.S. Pat. No. 4,654,300 (Zuk, et al.) describes a fluorescent microbead quenching assay.

U.S. Pat. No. 4,174,384 (Ullman, et al. II) describes fluorescence quenching with immunological pairs in immunoassays.

U.S. Pat. No. 4,193,983 (Ullman, et al. III) discloses labeled liposome particle compositions and immunoassays therewith.

U.S. Pat. Nos. 4,199,559 and 3,996,345 (Ullman, et al. IV and V) describes fluorescence quenching with immunological pairs in immunoassays.

O'Connell, et al., *Clin. Chem.*, (1985) 31(9), 1424–1426 discloses a colorimetric immunoassay for digoxin utilizing large, unilamellar phospholipid vesicles having dye entrapped in the aqueous phase of the liposome.

U.S. Pat. Nos. 3,850,578 (McConnell); 4,483,921 (Yaverbaum); and 4,483,929 (Szoka) disclose immunoreactive liposome reagents in which antigen or antibody is bound to the surface of lipid vesicles.

U.S. Pat. Nos. 4,529,561 (Hunt, et al.); 4,522,803 (Lenk, et al.); and 4,485,054 (Mezei, et al.) disclose a variety of methods for preparing lipid vesicles.

U.S. Pat. No. 4,311,712 (Evans, et al.) discloses a process for preparing a freeze dried liposome mixture.

U.S. Pat. No. 4,588,578 (Fountain, et al.) discloses a method for the preparation of monophasic lipid vesicles and the use of such vesicles for drug delivery systems.

U.S. Pat. No. 4,576,912 discloses a method of enhancing the fluorescent level of an immunoassay using certain long-chain carriers tagged with a plurality of fluorophores.

U.S. Pat. No. 4,891,324 describes a particle with luminescer for assays.

Selective killing of T lymphocytes by phototoxic liposomes is described by Yemu, et al. (1987) *Proc. Natl. Acad. Sci. USA*, 84: 246–250.

Mew, et al. in *J. of Immunology*, 130(3): 1473–1477 (1983) discloses photoimmunotherapy: treatment of animal tumors with tumor-specific monoclonal antibody-hematoporphyrin conjugates.

Optical microscopic observation of single small molecules is discussed by Hirschfeld (1976) *Applied Optics*, 15(12): 3135–3139.

European Patent Application 0 322 926 (McCapra, et al.) describes assays utilizing improved chemiluminescent esters, thioesters, and amides.

European Patent Application 0 352 713 (Schaap) describes a method and compositions providing enhanced chemiluminescence from 1,2-dioxetanes.

U.S. Pat. No. 4,978,614 (Bronstein) discloses a method of detecting a substance using enzymatically-induced decomposition of dioxetanes.

Bronstein, et al. (U.S. Pat. No. 4,956,477), discuss the synthesis of 1,2-dioxetanes.

Schaap, et al., describe enhanced luminescence from 1,2-dioxetanes through energy transfer to tethered fluorescers in WO 90/07511.

U.S. Pat. No. 4,959,182 (Schaap) discloses a method and compositions providing enhanced chemiluminescence from 1,2-dioxetanes.

U.S. Pat. No. 4,962,192 (Schaap) and 4,857,652 (Schaap) describe chemiluminescent 1,2-dioxetane compounds.

Bronstein, et al., describe a method using chemiluminescent 1,2-dioxetanes in U.S. Pat. No. 4,931,223.

The purification of stable water-soluble dioxetanes is disclosed in WO 90/02742 (Edwards, et al.).

Novel Chemiluminescent fused polycyclic ring-containing 1,2-dioxetanes and assays in which they are used are described in WO 90/00164 (Edwards, gal.)

WO 89/06226 (Edwards, et al.) discusses the synthesis of 1,2-dioxetanes and intermediates therefor.

Neckers, et al., describe polymer-bound photosensitizing catalysts in U.S. Pat. No. 4,315,998.

A method of detecting a substance using enzymatically-induced decomposition of dioxetanes is discussed in WO 88/00695 (Bronstein, et al.).

European Patent Application 0 324 202 (Zomer, et al.) discloses acridinium compounds as chemiluminogenic labels.

European Patent Application 0 144 914 (Alberella, et al.) describes a hybridization assay employing labeled pairs of hybrid binding reagents.

European Patent Application 0 401 001 (Urdea, et al.) describes chemiluminescent double-triggered 1,2-dioxetanes.

SUMMARY OF THE INVENTION

In its broadest aspect the present invention involves a method for determining a condition such as, for example, the presence or absence of (a) an analyte in a medium, (b) a leak in a fluidic system, (c) wear in a mechanical part or (d) emission of light. The method comprises irradiating a composition arising from or subject to the condition. The composition comprises a non-particulate solid matrix or a particulate matrix having incorporated therein (a) a photosensitizer capable upon irradiation of generating singlet oxygen and (b) a chemiluminescent compound capable of being activated by singlet oxygen. The particulate matrix may be solid or fluid.

In another aspect the invention concerns a method for labeling a material such as (a) a molecule that is related to the presence or amount of an analyte in a medium, (b) a fluidic material in a fluidic system or (c) abraded material from a mechanical part, (d) a cell, or (e) biological tissue. The method comprises combining with the material (1) a photosensitizer capable upon irradiation of generating singlet oxygen and (2) a chemiluminescent compound capable of being activated by singlet oxygen. The photosensitizer and the chemiluminescent compound are incorporated in a matrix that may be a non-particulate solid or a particulate solid or fluid.

Another aspect of the present invention is a method for detecting a material. The method comprises (a) combining with the material (1) a photosensitizer capable upon irradiation of generating singlet oxygen and (2) a chemiluminescent compound capable of being activated by singlet oxygen. The photosensitizer and the chemiluminescent compound are incorporated in a solid matrix or particulate solid or fluid, (b) irradiating the material with light of wavelength 200–1000 nm and (c) detecting light emitted by the chemiluminescent compound.

Another aspect of the present invention concerns a method for generating delayed luminescence. The method comprises the step of irradiating a composition comprising a non-particulate, solid matrix or particulate solid or fluid matrix having incorporated therein (1) a photosensitizer capable upon irradiation of generating singlet oxygen and (2) a chemiluminescent compound capable of being activated by singlet oxygen.

Another embodiment of the present invention is directed to a method for determining an analyte. The method comprises the steps of subjecting a medium suspected of containing an analyte to conditions under which a complex of specific binding pair (sbp) members is formed in relation to the presence of the analyte and determining whether the sbp member complex has formed by employing as a label a single composition having both chemiluminescent and photosensitizer properties such that upon activation of the photosensitizer property singlet oxygen is generated and activates the chemiluminescent property.

Another embodiment of a method for determining an analyte comprises (a) providing in combination (1) a medium suspected of containing said analyte, (2) a label reagent comprising a first specific binding pair (sbp) member associated with a single composition having both photosensitizer and chemiluminescent properties such that upon activation of the photosensitizer property singlet oxygen is generated and activates the chemiluminescent property, wherein the first sbp member is capable of binding to the analyte or to a second sbp member to form a complex related to the presence of the analyte, (b) activating the photosensitizer property and (c) detecting the amount of luminescence generated by the chemiluminescent property, the amount thereof being related to the amount of analyte in the medium.

Another method for determining an analyte in accordance with the present invention comprises (a) providing in combination (1) a medium suspected of containing the analyte, (2) a label reagent comprising a first specific binding pair (sbp) member associated with a particle having a photosensitizer capable upon activation of generating singlet oxygen and a chemiluminescent compound capable of being activated by singlet oxygen such that upon activation of the photosensitizer singlet oxygen is generated and activates the chemiluminescent compound, wherein the first sbp member is capable of binding to the analyte or to a second sbp member to form a complex related to the presence of the analyte, (b) activating the photosensitizer and (c) detecting the amount of luminescence generated by the chemiluminescent compound, the amount thereof being related to the amount of analyte in the medium.

Another embodiment of the invention is a composition comprising a non-particulate solid matrix or particulate solid or fluid having incorporated therein a photosensitizer capable upon activation of generating singlet oxygen and a chemiluminescent compound capable of being activated by singlet oxygen.

Another composition in accordance with the invention comprises a particle, either solid or fluid, having incorporated therein a photosensitizer capable of generating singlet oxygen and a chemiluminescent compound capable of being activated by singlet oxygen, wherein the particle is bound to a molecule useful in the detection of an analyte.

Another embodiment of the invention is a composition comprising fluid particles selected from the group consisting of oil droplets, liposomes and emulsions having incorporated therein a photosensitizer capable upon activation of generating singlet oxygen and a chemiluminescent compound capable of being activated by singlet oxygen.

Another embodiment of the present invention is a method for calibrating light intensity emitted by a luminescent composition, The method comprises the steps of (a) combining in a medium a luminescent composition capable of emitting light upon irradiation and one of the above compositions of the invention, wherein one of the compositions when activated by light has a decay time for light emission substantially greater than the decay time for the other, (b) irradiating the medium to activate the luminescent composition and the composition of the invention, (c) measuring the intensity of light emitted during the decay of the activated composition having the shorter decay time, (d) measuring the intensity of light emitted after the measuring of step (c) and after at least partial decay of the activated composition having the shorter decay time, and (e) comparing the intensity of the light emitted during the decay of the activated composition having the shorter decay time with the intensity of light emitted in step (d) to provide for internal calibration. Steps b and c may be repeated one or more times prior to step d. In one embodiment the activated composition of composition of the invention has the shorter decay time. Another embodiment of the present invention is a kit comprising one of the above compositions and a member of a specific binding pair.

DESCRIPTION OF THE SPECIFIC EMBODIMENTS

The present invention makes available compositions that are solid materials or solid or fluid particles comprised of a photosensitizer and a chemiluminescent compound. Irradiation of these compositions can yield delayed luminescence wherein the lifetime of the luminescent decay is determined by a number of factors including the structure of the chemiluminescent compound, the composition of the solid material or the particle, the temperature and the presence of activators that enhance the rate of decomposition of the molecules, usually dioxetanes, produced upon reaction of the chemiluminescent compound with singlet oxygen. The compositions are capable of luminescing, for example, when in the dry state, bound to cell surfaces, or in other media in which they are stable.

The compositions can be used, for example, as very sensitive tracers because they can be activated first and then detected seconds or minutes after the activation. For example, the compositions can be used to trace leaks in fluidic systems, when suspended in the fluid, which can be a liquid or a gas. Application of tracers to detect leaks is well-known in the art. In general, about $10^{-14}$–$10^{-2}$% of a composition of the invention is dispersed into the liquid or gas. Next, the fluid is irradiated with light to activate the photosensitizer and then the fluid is allowed to pass through the system. In this application it is desirable to delay the luminescence by using one of the techniques described below. The system is examined for any luminescence that might be escaping to determine whether any leak is present.

The compositions can also be utilized in forensic criminology as a dusting powder. The use of dusting powders for such purpose is very well-known and will not be described here. For this purpose the present compositions should be particulate and have a diameter of about 0.01–10 μm. The concentration of photosensitizer and chemiluminescent compound in the particle is generally about $10^{-5}$ M to $10^{-1}$ M.

Examples of other uses of the compositions of the invention are provided below by way of illustration and not limitation. The compositions can be incorporated in mechanical parts to permit assessment of wear by detection of abraded material. They may also be used as a light dosimeter or solid state fluorescence calibrator. When used as a dosimeter it will frequently be desirable for the dioxetane formed by the reaction of singlet oxygen with the chemiluminescent compound to be sufficiently stable so that luminescence will not occur until the composition is heated. Preferably, for these applications the composition is in the form of a film. The compositions may also be used to calibrate light sources and photometric devices. In general, the particulate compositions of the invention may be chosen to have relatively long decay times so that these values may be used to ratio against more rapid decay times of other materials and provide for calibration in light intensity measurements and photomultiplier applications.

The particulate compositions of the inventions find particular application in the field of diagnostic assays where they can be used as a label or as part of a labeled reagent. For the most part the composition will have a member of a specific binding pair (sbp) bound to its surface. The sbp member may be capable of binding to an analyte, or a molecule whose presence is indicative of the presence of an analyte, to form a complex. The complex can be detected by irradiating the label and monitoring light that is subsequently emitted. The assays can be carried out in a competitive or a sandwich mode or variations thereof.

Where the molecule to be detected involves a cell, the cell can be labeled with a particulate composition of the invention. For example, the composition of the invention can include an sbp member complementary to an sbp member on the surface of the cell. The labeled cell is irradiated and then visualized through a microscope without additional illumination. As a result background fluorescence, which is a serious problem in fluorescence microscopy, can be avoided.

The present compositions can be utilized for internal calibration in luminescent assays. By including particles of the composition in an assay medium in which luminescence is produced by irradiating the medium, the composition produces an emission that can be detectably different from that produced in the assay. This difference can be the result of a different wavelength emission or a different decay rate of the luminescence.

For example, in a fluorescence immunoassay the fluorescence intensity is measured first. Irradiation of the medium is discontinued and luminescence emanating from the composition of the invention is measured to provide an accurate internal reference of light intensity, detector sensitivity and sample interference. The compositions can be utilized in a similar manner for internal and external calibration in the assays described in U.S. Ser. No. 07/718,490 (the '490 application), the disclosure of which is incorporated herein by reference. In that regard, as mentioned above, the particulate compositions of the present invention may be chosen to have relatively long decay times when compared to the decay times for the materials of the '490 application. As a result the present particulate compositions may be used for internal calibration in assays utilizing the materials of the '490 application. A medium containing both the '490 materials and the particulate compositions of the present invention can be irradiated, the intensity of light emitted following irradiation can be measured, a sufficient time can be allowed to elapse to permit partial or complete decay of the emission from the '490 application materials, the medium can then be irradiated again and light intensity measured and the emission allowed to decay optionally and the process can be repeated a sufficient number of times to maximize the reliability of the measurement. Following the final cycle, the intensity of light which will now be emanating primarily from the present particulate composition can be independently measured because the decay times for the present particulate compositions are much longer. The residual light intensity emitted by the present particulate compositions over the course of the irradiations period is proportional to the irradiating light intensity times the irradiation time. The light intensities measured prior to decay of the emission '490 materials can be ratioed against the residual intensity of the present particulate compositions to provide for internal calibration. Conversely the present composition decay times could be shorter than the '490 composition decay times and the same procedure could be used for calibration except that the rapidly decaying light intensity would serve as a reference and the residual light intensity will be from the '490 materials.

Light intensity may vary widely. In general, for rapidly decaying species where irradiation can be carried out until a steady state is achieved, the brighter the light source, the more of the activated species is present at the steady state, and the more intense will be the subsequent emission. For slow decaying compositions, the longer the irradiation period, the more activated species accumulated and the more intense the emission. In this case one can trade off time of irradiation and light intensity. In the former case light intensity is critical. Irradiation may be carried out from 1 micro second to 20 minutes, preferably, 0.1 to 60 seconds, more preferably, 0.1 to 10 seconds, usually about 1 second. The light source can be multi-wavelength but is then filtered to cut off short wavelength light. For example, a 650 cutoff filter with a tungsten-halogen lamp (100 to 1,000 watts) can be used. Alternatively, a He/Ne laser source can be utilized. Another approach involves the use of an LED, usually 630 nm or longer with 5 to 100 m watts output. The experiments described hereinbelow in the specification use a 400 watt halogen lamp light piped directly to the sample.

An assay for an analyte may be accomplished by separating a particulate composition of the invention used as a label, to which has become bound an analyte or an sbp member whose presence is indicative of the presence of an analyte, from unbound composition. Either the separated bound or unbound fraction is treated to activate the photosensitizer, usually by irradiation with light, and the fraction is then examined for luminescence. The emission of the chemiluminescent compound can be modified by a catalyst and/or energy acceptor, which can be included in the compositions of the invention. The energy acceptor must be fluorescent and will usually modify the wavelength of the emission. The catalyst will usually increase the rate and/or efficiency of emission. The fluorescent and catalytic properties may be present in the same compound or in separate compounds, one or both of which may be included in the compositions of the invention.

The subject assay provides for a convenient method for detecting and measuring a wide variety of analytes in a simple, efficient, reproducible manner, which can employ visual inspection or conventional equipment for measuring the amount of light produced during the reaction.

Before proceeding further with a description of the specific embodiments of the present invention, a number of terms will be defined and described in detail.

Analyte—the compound or composition to be detected. The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

The following are classes of proteins related by structure: protamines histones
albumins
globulins
scleroproteins
phosphoproteins
mucoproteins
chromoproteins
lipoproteins
nucleoproteins
glycoproteins
T-cell receptors
proteoglycans
HLA
unclassified proteins, e.g., somatotropin, prolactin, insulin, pepsin A number of proteins found in the human plasma are important clinically and include:

Prealbumin
Albumin
$\alpha_1$-Lipoprotein
$\alpha_1$-Antitrypsin
$\alpha_1$-Glycoprotein
Transcortin
4.6S-Postalbumin
Tryptophan-poor $\alpha_1$-glycoprotein
$\alpha_1$X-Glycoprotein
Thyroxin-binding globulin
Inter-$\alpha$-trypsin-inhibitor
Gc-globulin (Gc 1-1)
(GC 2-1)
(GC 2-2)
Haptoglobin
(Hp 1-1)
(Hp 2-1)
(Hp 2-2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G (IgG) or $\gamma$G-globulin
Mol. formula:

$\gamma 2k2$ or $\gamma 2\lambda 2$

Immunoglobulin A (IgA) or $\gamma$A-globulin
Mol. formula:

$(\alpha_2\kappa_2)^n$ or $(\alpha_2\kappa_2)^n$

Immunoglobulin M (IgM) or $\gamma$M-globulin
Mol. formula:

$(\mu_2\kappa_2)^5$ or $(\mu_2\lambda_2)^5$

Immunoglobulin D (IgD) or $\gamma$D-Globulin ($\gamma$D)
Mol. formula:

$(\delta_2\kappa_2)$ or $\delta_2\lambda_2$

Immunoglobulin E (IgE) or $\gamma$E-Globulin ($\gamma$E)
Mol. formula:

$(\epsilon_2\kappa_2)$ or $(\epsilon_2\lambda_2)$

Free $\kappa$ and $\lambda$ light chains
Complement factors:
C'1
  C'1q
  C'1r
  C'1s
C'2
C'3
  $\beta_1$A
  $\alpha_2$D
C'4
C'5
C'6
C'7
C'8
C'9

Important blood clotting factors include:

| International designation | Name |
| --- | --- |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:

| Peptide and Protein Hormones |
| --- |
| Parathyroid hormone (parathromone) |
| Thyrocalcitonin |
| Insulin |
| Glucagon |
| Relaxin |
| Erythropoietin |
| Melanotropin (melancyte-stimulating) hormone; intermedin) |
| Somatotropin (growth hormone) |
| Corticotropin (adrenocorticotropic hormone) |
| Thyrotropin |
| Follicle-stimulating hormone |
| Luteinizing hormone (interstitial cell-stimulating hormone) |
| Luteomammotropic hormone (luteotropin, prolactin |

Gonadotropin
(chorionic gonadotropin)
Tissue Hormones

Secretin
Gastrin
Angiotensin I and II
Bradykinin
Human placental lactogen
Cytokines IL I
IL II
IL VI
EGF
TNF
NGF
Cancer Antigens PSA
CEA
α-fetoprotein Acid phosphatase
CA19.9
CA125
Tissue Specific Antigens alkaline phosphatase
myoglobin
CPK-MB
calcitonin
Myelin basic protein
Peptide Hormones from the Neurohypophysis Oxytocin
Vasopressin
Releasing factors (RF)
CRF, LRF, TRF, Somatotropin-RF,
GRF, FSH-RF, PIF, MIF Other polymeric materials of interest are mucopolysaccharides and polysaccharides.

Illustrative microorganisms include:

| | |
|---|---|
| Corynebacteria | |
| *Corynebacterium diphtheria* | |
| Pneumococci | |
| *Diplococcus pneumoniae* | |
| Streptococci | |
| *Streptococcus pyrogenes* | |
| *Streptococcus salivarus* | |
| Staphylococci | |
| *Staphylococcus aureus* | |
| *Staphylococcus albus* | |
| Neisseria | |
| *Neisseria meningitidis* | |
| *Neisseria gonorrhea* | |
| Enterobacteriaciae | |
| *Escherichia coli* | |
| *Aerobacter aerogenes* | The coliform |
| *Klebsiella pneumoniae* | bacteria |
| *Salmonella typhosa* | |
| *Salmonella choleraesuis* | The Salmonellae |
| *Salmonella typhimurium* | |
| *Shigella dysenteria* | |
| *Shigella schmitzii* | |
| *Shigella arabinotarda* | |
| | The Shigellae |
| *Shigella flexneri* | |
| *Shigella boydii* | |
| *Shigella sonnei* | |
| Other enteric bacilli | |
| *Proteus vulgaris* | |
| *Proteus mirabilis* | Proteus species |
| *Proteus morgani* | |
| *Pseudomonas aeruginosa* | |
| *Alcaligenes faecalis* | |
| *Vibrio cholerae* | |
| Hemophilus-Bordetella group | *Rhizopus oryzae* |
| *Hemophilus influenza, H. ducryi* | *Rhizopus arrhizua* |
| | Phycomycetes |
| *Hemophilus hemophilus* | *Rhizopus nigricans* |
| *Hemophilus aegypticus* | *Sporotrichum schenkii* |
| *Hemophilus parainfluenza* | *Flonsecaea pedrosoi* |
| *Bordetella pertussis* | *Fonsecacea compact* |
| Pasteurellae | *Fonsecacea dermatidis* |
| *Pasteurella pestis* | *Cladosporium carrionii* |
| *Pasteurella tulareusis* | *Phialophora verrucosa* |
| Brucellae | *Aspergillus nidulans* |
| *Brucella melitensis* | *Madurella mycetomi* |
| *Brucella abortus* | *Madurella grisea* |
| *Brucella suis* | *Allescheria boydii* |
| Aerobic Spore-forming Bacilli | *Phialophora jeanselmei* |
| *Bacillus anthracis* | *Microsporum gypseum* |
| *Bacillus subtilis* | *Trichophyton mentagrophytes* |
| *Bacillus megaterium* | *Keratinomyces ajelloi* |
| *Bacillus cereus* | *Microsporum canis* |
| Anaerobic Spore-forming Bacilli | *Trichophyton rubrum* |

| | |
|---|---|
| Clostridium botulinum | Microsporum adouini |
| Clostridium tetani | Viruses |
| Clostridium perfringens | Adenoviruses |
| Clostridium novyi | Herpes Viruses |
| Clostridium septicum | Herpes simplex |
| Clostridium histolyticum | Varicella (Chicken pox) |
| Clostridium tertium | Herpes Zoster (Shingles) |
| Clostridium bifermentans | Virus B |
| Clostridium sporogenes | Cytomegalovirus |
| Mycobacteria | Pox Viruses |
| Mycobacterium tuberculosis hominis | Variola (smallpox) |
| Mycobacterium bovis | Vaccinia |
| Mycobacterium avium | Poxvirus bovis |
| Mycobacterium leprae | Paravaccinia |
| Mycobacterium paratuberculosis | Molluscum contagiosum |
| Actinomycetes (fungus-like bacteria) | Picornaviruses |
| Actinomyces Isaeli | Poliovirus |
| Actinomyces bovis | Coxsackievirus |
| Actinomyces naeslundii | Echoviruses |
| Nocardia asteroides | Rhinoviruses |
| Nocardia brasiliensis | Myxoviruses |
| The Spirochetes | Influenza(A, B, and C) |
| Treponema pallidum   Spirillum minus | Parainfluenza (1–4) |
| Treponema pertenue   Streptobacillus monoiliformis | Mumps Virus |
| | Newcastle Disease Virus |
| Treponema carateum | Measles Virus |
| Borrelia recurrentis | Rinderpest Virus |
| Leptospira icterohemorrhagiae | Canine Distemper Virus |
| Leptospira canicola | Respiratory Syncytial Virus |
| Trypanasomes | Rubella Virus |
| Mycoplasmas | Arboviruses |
| Mycoplasma pneumoniae | |
| Other pathogens | Eastern Equine Encephalitis Virus |
| Listeria monocytogenes | Western Equine Encephalitis Virus |
| Erysipelothrix rhusiopathiae | Sindbis Virus |
| Streptobacillus moniliformis | Chikugunya Virus |
| Donvania granulomatis | Semliki Forest Virus |
| Bartonella bacilliformis | Mayora Virus |
| Rickettsiae (bacteria-like parasites) Virus | St. Louis Encephalitis |
| Rickettsia prowazekii | California Encephalitis Virus |
| Rickettsia mooseri | Colorado Tick Fever Virus |
| Rickettsia rickettsii | Yellow Fever Virus |
| Rickettsia conori | Dengue Virus |
| Rickettsia australis | Reoviruses |
| Rickettsia sibiricus | Reovirus Types 1–3 |
| | Retroviruses |
| Rickettsia akari | Human Immunodeficiency |
| Rickettsia tsutsugamushi | Viruses I and II (HIV) |
| | Human T-cell Lymphotrophic Virus I & II (HTLV) |
| Rickettsia burnetti | Hepatitis |
| Rickettsia quintana | Hepatitis A Virus |
| Chlamydia (unclassifiable parasites bacterial/viral) | Hepatitis B Virus |
| Chlamydia agents (naming uncertain) | Hepatitis C Virus |
| Fungi | Tumor Viruses |
| Cryptococcus neoformans | Rauscher Leukemia Virus |
| Blastomyces dermatidis | Gross Virus |
| Hisoplasma capsulatum | Maloney Leukemia Virus |
| Coccidioides immitis | Human Papilloma Virus |
| Paracoccidioides brasiliensis | |
| Candida albicans | |
| Aspergillus fumigatus | |
| Mucor corymbifer (Absidia corymbifera) | |

The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids. Among the alkaloids are morphine alkaloids, which includes morphine, codeins, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The next group of drugs includes steroids, which includes the estrogens, androgens, and reocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines; catecholamines, which includes ephedrine, L-dopa, epinephrine; narceine; papaverine; and metabolites of the above.

The next group of drugs is benzheterocyclics which include oxazepam, chlorpromazine, tegretol, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs is the hormones such as thyroxine, cortisol, triiodothyronine, testosterone, estradiol, estrone, progestrone, polypeptides such as angiotensin, LHRH, and immunosuppresants such as cyclosporin, FK506, mycophenolic acid, and so forth.

The next group of drugs includes the vitamins such as A, B, e.g. B12, C, D, E and K, folic acid, thiamine.

The next group of drugs is prostaglandins, which differ by the degree and sites of hydroxylation and unsaturation.

The next group of drugs is the tricyclic antidepressants, which include imipramine, dismethylimipramine, amitriptyline, nortriptyline, protriptyline, trimipramine, chlomipramine, doxepine, and desmethyldoxepin.

The next group of drugs are the anti-neoplastics, which include methotrexate.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as biological tissue, including body fluids, from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The biological tissue includes excised tissue from an organ or other body part of a host and body fluids, for example, urine, blood, plasma, serum, saliva, semen, stool, sputum, cerebral spinal fluid, tears, mucus, and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Polynucleotide—a compound or composition which is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. The polynucleotide includes nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g.., bacteria, yeasts, viruses, viroids, molds, fungi, plants, animals, humans, and fragments thereof, and the like.

Ligand—any organic compound for which a receptor naturally exists or can be prepared.

Ligand analog—a modified ligand, an organic radical or analyte analog, usually of a molecular weight greater than 100, which can compete with the analogous ligand for a receptor, the modification providing means to join a ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Specific binding—the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme—substrate interactions, polynucleotide interactions, and so forth.

Non-specific binding—non-covalent binding between molecules that is relatively independent of specific surface structures. Non-specific binding may result from several factors including hydrophobic interactions between molecules.

Antibody—an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sere (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7:1–24 (1975); Broughton and Strong, Clin. Chem. 22:726–732 (1976); and Playfair, et al., Br. Med. Bull. 30:24–31 (1974).

Antibodies can also be obtained by somatic cell hybridization techniques, such antibodies being commonly referred to as monoclonal antibodies. Monoclonal antibodies may be produced according to the standard techniques of Köhler and Milstein, *Nature* 265:495–497, 1975. Reviews of monoclonal antibody techniques are found in Lymphocyte Hybridomas, ed. Melchers, et al. Springer-Verlag (New York 1978), Nature 266:495 (1977), Science 208:692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milsrein, supra).

In another approach for the preparation of antibodies the sequence coding for antibody binding sites can be excised from the chromosome DNA and inserted into a cloning vector which can be expressed in bacteria to produce recombinant proteins having the corresponding antibody binding sites.

In general, antibodies can be purified by known techniques such as chromatography, e.g., DEAE chromatography, ABx chromatography, and the like, filtration, and so forth.

Alkyl—a monovalent branched or unbranched radical derived from an aliphatic hydrocarbon by removal of one H atom; includes both lower alkyl and upper alkyl.

Lower alkyl—alkyl containing from 1 to 5 carbon atoms such as, e.g., methyl, ethyl, propyl, butyl, isopropyl, isobutyl, pentyl, isopentyl, etc.

Upper alkyl—alkyl containing more than 6 carbon atoms, usually 6 to 20 carbon atoms, such as, e.g., hexyl, heptyl, octyl, etc.

Alkylidene—a divalent organic radical derived from an aliphatic hydrocarbon, such as, for example, ethylidene, in which 2 hydrogen atoms are taken from the same carbon atom.

Aryl—an organic radical derived from an aromatic hydrocarbon by the removal of one atom and containing one, or more aromatic rings, usually one to four aromatic rings, such as, e.g., phenyl (from benzene), naphthyl (from naphthalene), etc.

Aralkyl—an organic radical having an alkyl group to which is attached an aryl group, e.g., benzyl, phenethyl, 3-phenylpropyl, 1-naphthylethyl, etc.

Alkoxy—an alkyl radical attached to the remainder of a molecule by an oxygen atom, e.g., methoxy, ethoxy, etc.

Aryloxy—an aryl radical attached to the remainder of a molecule by an oxygen atom, e.g., phenoxy, naphthoxy, etc.

Aralkoxy—an aralkyl radical attached to the remainder of a molecule by an oxygen atom, e.g., benzoxy, 1-naphthylethoxy, etc.

Substituted—means that a hydrogen atom of a molecule has been replaced by another atom, which may be a single atom such as a halogen, etc., or part of a group of atoms forming a functionality such as a substituent having from 1 to 50 atoms (other than the requisite hydrogen atoms necessary to satisfy the valencies of such atoms), which atoms are independently selected from the group consisting of carbon, oxygen, nitrogen, sulfur, halogen (chlorine, bromine, iodine, fluorine) and phosphorus, and which may or may not be bound to one or more metal atoms.

Alkylthio—an alkyl radical attached to the remainder of a molecule by a sulfur atom, e.g., methylthio, ethylthio, etc.

Arylthio—an aryl radical attached to the remainder of a molecule by a sulfur atom, e.g., phenylthio, naphthylthio, etc.

Electron-donating group—a substituent which when bound to a molecule is capable of polarizing the molecule such that the electron-donating group becomes electron poor and positively charged relative to another portion of the molecule, i.e., has reduced electron density. Such groups may be, by way of illustration and not limitation, amines, ethers, thioethers, phosphines, hydroxy, oxyanions, mercaptans and their anions, sulfides, etc.

A substituent having from 1 to 50 atoms (other than the requisite hydrogen atoms necessary to satisfy the valencies of such atoms), which atoms are independently selected from the group consisting of carbon, oxygen, nitrogen, sulfur, halogen and phosphorus—an organic radical; the organic radical has 1 to 50 atoms other than the requisite number of hydrogen atoms necessary to satisfy the valencies of the atoms in the radical. Generally, the predominant atom is carbon (C) but may also be oxygen (O), nitrogen (N), sulfur (S), phosphorus (P), wherein the O, N, S, or P, if present, are bound to carbon or one or more of each other or to hydrogen or a metal atom to form various functional groups, such as, for example, carboxylic acids, alcohols, thiols, carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes, nitriles, and the like. Illustrative of such organic radicals or groups, by way of illustration and not limitation, are alkyl, alkylidine, aryl, aralkyl, and alkyl, aryl, and aralkyl substituted with one or more of the aforementioned functionalities.

Linking group—the covalent linkage between molecules. The linking group will vary depending upon the nature of the molecules, i.e., photosensitizer, chemiluminescent compound, sbp member or molecule associated with or part of a particle, being linked. Functional groups that are normally present or are introduced on a photosensitizer or chemiluminescent compound will be employed for linking these materials to an sbp member or a particle such as a lipophilic component of a liposome or oil droplet, latex particle, silicon particle, metal sol, or dye crystallite.

For the most part, carbonyl functionalities will find use, both oxocarbonyl, e.g., aldehyde and non-oxocarbonyl (including nitrogen and sulfur analogs) e.g., carboxy, amidine, amidate, thiocarboxy and thionocarboxy.

Alternative functionalities of oxo include active halogen, diazo, mercapto, olefin, particularly activated olefin, amino, phosphoro and the like. A description of linking groups may be found in U.S. Pat. No. 3,817,837, which disclosure is incorporated herein by reference.

The linking groups may vary from a bond to a chain of from 1 to 100 atoms, usually from about 1 to 70 atoms, preferably 1 to 50 atoms more preferably 1 to 20 atoms, each independently selected from the group normally consisting of carbon, oxygen, sulfur, nitrogen, halogen and phosphorous. The number of heteroatoms in the linking groups will normally range from about 0 to 20, usually from about 1 to 15, more preferably 2 to 6. The atoms in the chain may be substituted with atoms other than hydrogen in a manner similar to that described for the substituent having from 1 to 50 atoms. As a general rule, the length of a particular linking group can be selected arbitrarily to provide for convenience of synthesis and the incorporation of any desired group such as an energy acceptor, fluorophor, group for analysis of intersystem crossing such as a heavy atom, and the like. The linking groups may be aliphatic or aromatic, although with diazo groups, aromatic groups will usually be involved.

When heteroatoms are present, oxygen will normally be present as oxo or oxy, bonded to carbon, sulfur, nitrogen or phosphorous, nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, when a linking group is bound to the photosensitizer, the photochemically activatable chemiluminescent compound or a particulate composition of the invention will have a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α, β-unsaturated ester. These functionalities will be linked to amine groups, carboxyl groups, active olefins, alkylating agents, e.g., bromoacetyl. Where an amine and carboxylic acid or its nitrogen derivative or phophoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed.

A group or functionality imparting hydrophilicity or water solubility—is a hydrophilic functionality, which increases wettability of solids with water and the solubility in water of compounds to which it is bound. Such functional group or functionality can be a substituent having 1 to 50 or more atoms and can include a sulfonate, sulfate, phosphate, amidine, phosphonate, carboxylate, hydroxyl particularly polyols, amine, ether, amide, and the like. Illustrative functional groups are carboxyalkyl, sulfonoxyalkyl, $CONHOCH_2COOH$, CO-(glucosamine), sugars, dextran, cyclodextrin, $SO_2NHCH_2COOH$, $SO_3H$, $CONHCH_2CH_2SO_3H$, $PO_3H_2$, $OPO_3H_2$, hydroxyl, carboxyl, ketone, and combinations thereof. Most of the above functionalities can also be utilized as attaching groups, which permit attachment of an sbp member to a particulate composition comprised of the photosensitizer and chemiluminescent compound.

A group or functionality imparting lipophilicity or lipid solubility—is a lipophilic functionality, which decreases the wettability of surfaces by water and the solubility in water of compounds to which it is bound. Such functional group or functionality can contain 1 to 50 or more atoms, usually carbon atoms substituted with hydrogen or halogen and can include alkyl, alkylidene, aryl and aralkyl. The lipophilic group or functionality will normally have one to six straight or branched chain aliphatic groups of at least 6 carbon atoms, more usually at least 10 carbon atoms, and preferably at least 12 carbon atoms, usually not more than 30 carbon atoms. The aliphatic group may be bonded to rings of from 5 to 6 members, which may be alicyclic, heterocyclic, or aromatic. Lipophilic groups may be bonded to photosensitizers or chemiluminescent compounds to increase their solubility in a non-aqueous matrix.

Photosensitizer—a sensitizer for generation of singlet oxygen usually by excitation with light. Usually, the photosensitizer absorbs at a longer wavelength than the chemiluminescent compound and has a lower energy triplet than the chemiluminescent compound, although neither is critical for the successful operation of the present invention. The photosensitizer can be photoactivatable (e.g., dyes and aromatic compounds). The photosensitizer is usually a compound comprised of covalently bonded atoms, usually with multiple conjugated double or triple bonds. The compound should absorb light in the wavelength range of 200–1100 nm, usually 300–1000 nm, preferably 450–950 nm, with an extinction coefficient at its absorbance maximum greater than 500 $M^{-1}cm^{-1}$, preferably at least 5000 $M^{-1}cm^{-1}$, more preferably at least 50,000 $M^{-1}cm^{-1}$ at the excitation wavelength. The lifetime of an excited state produced following absorption of light in the absence of oxygen will usually be at least 100 nsec, preferably at least 1 msec. In general, the lifetime must be sufficiently long to permit energy transfer to oxygen, which will normally be present at concentrations in the range of $10^{-5}$ to $10^{-3}M$ depending on the medium. The photosensitizer excited state will usually have a different spin quantum number (S) than its ground state and will usually be a triplet (S=1) when, as is usually the case, the ground state is a singlet (S=O). Preferably, the photosensitizer will have a high intersystem crossing yield. That is, photoexcitation of a photosensitizer will produce the long lived state (usually triplet) with an efficiency of at least 10%, desirably at least 40%, preferably greater than 80%. The excited state will usually have an energy relative to the ground state of at least 20 Kcal/mole, preferably at least 22 Kcal/mole and usually less than about 65 Kcal/mole although higher energies can be used. The photosensitizer is usually at most weakly fluorescent under the assay conditions (quantum yield usually less that 0.5, preferably less that 0.1).

Photosensitizers that are to be excited by light will be relatively photostable and will not chemically react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3–6 of the periodic table, especially iodine or bromine, or they may have extended aromatic structures. Typical photosensitizers include acetone, benzophenone, 9-thioxanthone, eosin, 9,10-dibromoanthracene, methylene blue, metallo-porphyrins, such as hematoporphyrin, phthalocyanines, chlorophylis, rose bengal, buckminsterfullerene, etc., and derivatives of these compounds having substituents of 1 to 50 atoms for rendering such compounds more lipophilic or more hydrophilic and/or as attaching groups for attachment, or example, to an sbp member. Examples of other photosensitizers that may be utilized in the present invention are those that have the above properties and are enumerated in N.J. Turro, "Molecular Photochemistry", page 132, W. A. Benjamin Inc., N.Y. 1965.

The photosensitizers are preferably relatively non-polar to assure dissolution into a lipophilic member when the photosensitizer is incorporated in an oil droplet, liposome, latex particle, etc.

The photosensitizer assists photoactivation where activation is by singlet oxygen. Usually, the photosensitizer absorbs light and the thus formed excited photosensitizer activates oxygen to produce singlet oxygen, which reacts with the chemiluminescent compound to give a metastable luminescent intermediate. Desirably, no addition of chemical reagents is required to activate the present compositions and the photosensitizer and the chemiluminescent compound are found within one composition.

A photosensitizer can be employed in a number of different approaches to produce singlet oxygen, which activates the chemiluminescent compound. The photosensitizer may be dissolved in or bound to a particle, which further may be bound to an sbp member. Generally, the amount of photosensitizer employed is that sufficient to produce a concentration of singlet oxygen that results in activation of the chemiluminescent compound.

Solid matrix—a support or surface comprised of a porous or non-porous water insoluble material. The surface can have any one of a number of shapes, such as strip, rod, particle, including bead, and the like. The surface can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like.

Binding of sbp members to the support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970).

The surface will usually be polyfunctional or be capable of being polyfunctionalized or be capable of binding an oligonucleotide, an sbp member, a photosensitizer, and/or a photochemically activatable chemiluminescent compound through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature. See for example Cautrecasas, *J. Biol. Chem.* 245,3059 (1970). The length of a linking group to the oligonucleotide or sbp member may vary widely, depending upon the nature of the compound being linked, the effect of the distance between the compound being linked and the surface on the specific binding properties and the like.

Particles—particles of at least about 20 nm and not more than about 20 microns, usually at least about 40 nm and less than about 10 microns, preferably from about 0.10 to 2.0 microns diameter, normally having a volume of less than 1 picoliter. The particle may be organic or inorganic, swellable or non-swellable, porous or non-porous, solid or fluid, having any density, but preferably of a density approximating water, generally from about 0.7 to about 1.5 g/ml, preferably suspendible in water, and composed of material that can be transparent, partially transparent, or opaque. The particles may or may not have a charge, and when they are charged, they are preferably negative. The particles may be solid (e.g., polymer, metal, glass, organic and inorganic such as minerals, salts and diatoms), oil droplets (e.g., hydrocarbon, fluorocarbon, silicon fluid), or vesicles (e.g., synthetic such as phospholipid or natural such as cells and organelles). The particles may be latex particles or other particles comprised of organic or inorganic polymers; lipid bilayers, e.g., liposomes, phospholipid vesicles; oil droplets; silicon particles; metal sols; cells; polysaccharides; hydrogels; crosslinked proteins; diatoms; and dye crystallites.

The organic particles will normally be polymers, either addition or condensation polymers, which are readily dispersible in the assay medium. The organic particles will also be adsorptive or functionalizable so as to bind at their surface, either directly or indirectly, an sbp member and to bind at their surface or incorporate within their volume a photosensitizer or a photochemically activatable chemiluminescent compound.

The particles can be derived from naturally occurring materials, naturally occurring materials which are synthetically modified and synthetic materials. Natural or synthetic assemblies such as lipid bilayers, e.g., liposomes and non-phospholipid vesicles, are preferred. Among organic polymers of particular interest are polysaccharides, particularly cross-linked polysaccharides, such as agarose, which is available as Sepharose, dextran, available as Sephadex and Sephacryl, cellulose, starch, and the like; addition polymers, such as polystyrene, polyacrylamide, homopolymers and copolymers of derivatives of acrylate and methacrylate, particularly esters and amides having free hydroxyl functionalities including hydrogels, and the like. Inorganic polymers include silicones, glasses, available as Bioglas, and the like. Sols include gold, silver selenium, and other metals. Particles may also be dispersed water insoluble dyes such as porphyrins, phthalocyanines, etc., which may also act as photosensitizers. Particles may also include diatoms, cells, viral particles, magnetosomes, cell nuclei and the like.

Where the particles are commercially available, the particle size may be varied by breaking larger particles into smaller particles by mechanical means, such as grinding, sonication, agitation, etc.

The particles will usually be polyfunctional or be capable of being polyfunctionalized or be capable of being bound to an sbp member and/or being capable of being bound to a photosensitizer and/or chemiluminescent compound through specific or non-specific covalent or non-covalent interactions. A wide variety of functional groups are available or can be incorporated. Exemplary functional groups include carboxylic acids, aldehydes, amino groups, cyano groups, ethylene groups, hydroxyl groups, mercapto groups and the like. When covalent attachment of a sbp member, chemiluminescent compound or photosensitizer to the particle is employed, the manner of linking is well known and is amply illustrated in the literature. See for example Cautrecasas, *J. Biol. Chem.*, 245:3059 (1970). The length of a linking group may vary widely, depending upon the nature of the compound being linked, the nature of the particle, the effect of the distance between the compound being linked and the particle on the binding of sbp members and the analyte and the like.

When not covalently bound to the particle, the photosensitizer and/or photoactivatable chemiluminescent compound can be chosen to dissolve in or noncovalently bind to the surface of particles. In this case these compounds will preferably be hydrophobic to reduce their ability to dissociate from the particle. In general the particle composition is chosen so as to favor association of the photosensitizer and the chemiluminescent compound with the particle.

The number of photosensitizer or photoactivatable chemiluminescent compound molecules associated with a particle will on the average usually be at least one and may be sufficiently high that the particle consists entirely of photosensitizer and photochemically activatable chemiluminescent compound molecules. The preferred number of molecules will be selected empirically to provide the highest signal to background for the particular use such as an assay. In some cases this will be best achieved by associating a multiplicity of different photosensitizer molecules to particles or a multiplicity of the same or different fluorescent dye molecules that are capable of transferring energy to a photosensitizer can be incorporated into the particles to collect light energy and transfer it to photosensitizer molecules. Usually, the photosensitizer or photoactivatable chemiluminescent compound to sbp member ratio in the particles should be at least 0.1, preferably at least 10, and most preferably over 100 to 1.

Oil droplets—are fluid particles comprised of a lipophilic compound coated and stabilized with an emulsifier that is an amphiphilic molecule such as, for example, phospholipids, sphingomyelin, albumin and the like.

The phospholipids are based upon aliphatic carboxylic acid esters of aliphatic polyols, where at least one hydroxylic group is substituted with a carboxylic acid ester of from about 8 to 36, more usually of from about 10 to 20 carbon atoms, which may have from 0 to 3, more usually from 0 to 1 site of ethylenic unsaturation and at least 1, normally only 1, hydroxyl group substituted with phosphate to form a phosphate ester. The phosphate group may be further substituted with small aliphatic compounds which are of di or higher functionality, generally having hydroxyl or amino groups.

The oil droplets can be made in accordance with conventional procedures by combining the appropriate lipophilic compounds with a surfactant, anionic, cationic or nonionic, where the surfactant is present in from about 0.1 to 5, more usually from about 0.1 to 2 weight percent of the mixture and subjecting the mixture in an aqueous medium to agitation, such as sonication or vortexing. Illustrative lipophilic compounds include hydrocarbon oils, halocarbons including fluorocarbons, alkyl phthalates, trialkyl phosphates, triglycerides, etc.

An sbp member will usually be adsorbed to the surface of the oil droplet or bonded directly or indirectly to a surface component of the oil droplet. The sbp member may be incorporated into the liquid particles either during or after the preparation of the liquid particles. The sbp member will normally be present in from about 0.5 to 100, more usually 1 to 90, frequently from about 5 to 80 and preferably from about 50 to 100 mole percent of the molecules present on the surface of the particle.

The following is a list, by way of illustration and not limitation, of amphiphilic compounds, which may be utilized for stabilizing oil droplets: phosphatidyl ethanolamine, phosphatidyl choline, phosphatidyl serine, dimyristoylphosphatidyl choline, egg phosphatidyl choline, diapalmitoylphosphatidyl choline, phosphatidic acid, cardiolipin, lecithin, galactocerebroside, sphingomyelin, dicetylphosphate, phosphatidyl inositol, 2-trihexadecylammoniumethylamine, 1,3-bis(octadecyl phosphate)-propanol, stearoyloxyethylene phosphate, phospholipids, dialkylphosphates, sodium dodecyl sulfate, cationic detergents, anionic detergents, proteins such as albumin, non-ionic detergents, etc.

Other compounds may also be used which have lipophilic groups and which have been described previously. For the most part, these compounds will be alkylbenzenes, having alkyl groups of from 6 to 20 carbon atoms, usually mixtures of alkyl groups, which may be straight or branched chain, and having a carboxyl group, an hydroxylic group, a polyoxy alkylene group (alkylene of from 2 to 3 carbon atoms), carboxylic group, sulfonic acid group, or amino group. Aliphatic fatty acids may be used which will normally be of from about 10 to 36, more usually of from about 12 to 20 carbon atoms. Also, fatty alcohols having the carbon limits indicated for the fatty acids, fatty amines of similar carbon limitations and various steroids may also find use.

The oil droplets can comprise a fluorocarbon oil or a silicone oil (silicon particle). Such droplets are described by Giaever in U.S. Pat. Nos. 4,634,681 and 4,619,904 (the disclosures of which are incorporated herein in their entirety). These droplets are formed by dispersing a fluorocarbon oil or silicone oil in an aqueous phase. The droplets are prepared by placing a small amount of the selected oil (generally, such oils are commercially available) in a container with a larger amount of the aqueous phase. The liquid system is subjected to agitation to bring about emulsification and then centrifuged. The homogeneous phase is removed and the residual droplets are resuspended in an aqueous buffered medium. The above centrifugation and decantation steps can be repeated one or more times before the droplets are utilized.

Sbp members can be bound to the droplets in a number of ways. As described by Giaever, the particular sbp member, particularly a proteinoceous sbp member, can be coated on the droplets by introducing an excess of the sbp member into the aqueous medium prior to or after the emulsification step. Washing steps are desirable to remove excess sbp member. Functionalization of the oil introduces functionalities described above for linking to sbp members. Such functionalities can also be employed to link the droplets to a photosensitizer and/or a chemiluminescent compound. On the other hand, the photosensitizer and/or chemiluminescent compound can frequently be chosen to be soluble in the oil phase of the oil droplet and is not covalently bound. When the oil is a fluorocarbon, a fluorinated photosensitizer or chemiluminescent compound is often more soluble than the corresponding unfluorinated derivation.

Other oil droplets described by Giaever also find use in the present invention.

Liposomes—microvesicles of approximately spherical shape and are one of the preferred materials for use in the present invention. The liposomes have a diameter that is at least about 20 nm and not more than about 20 microns, usually at least about 40 nm and less than about 10 microns. Preferably, the diameter of the liposomes will be less than about two microns so as to limit settling or floatation.

The outer shell of a liposome consists of an amphiphilic bilayer that encloses a volume of water or an aqueous solution. Liposomes with more than one bilayer are referred to as multilamellar vesicles. Liposomes with only one bilayer are called unilamellar vesicles. Multilamellar vesicles are preferred in the present invention when using a lipophilic photosensitizer or chemiluminescent compound because of their ability to incorporate larger quantities of these materials than unilamellar vesicles. The amphiphilic bilayer is frequently comprised of phospholipids. Phospholipids employed in preparing particles utilizable in the present invention can be any phospholipid or phospholipid mixture found in natural membranes including lecithin, or synthetic glyceryl phosphate diesters of saturated or unsaturated 12-carbon or 24-carbon linear fatty acids wherein the phosphate can be present as a monoester, or as an ester of a polar alcohol such as ethanolamine, choline, inositol, serine, glycerol and the like. Particularly preferred phospholipids include L-a-palmitoyl oleoyl-phosphatidylcholine (POPC), palmitoyl oleoylphosphatidyl-glycerol (POPG), L-a-dioleoylphosphatidylglycerol, L-a(dioleoyl)-phosphatidyl ethanolamine (DOPE) and L-a(dioleoyl)-phosphatidyl—$^{(4\text{-}maleimidomethyl)}$—cyclohexane-1-carboxyamido)ethanol (DOPE-MCC).

The phospholipids in the bilayer may be supplemented with cholesterol and may be replaced with other amphiphilic compounds that have a polar head group, usually charged, and a hydrophobic portion usually comprised of two linear hydrocarbon chains. Examples of such substitutents include dialkylphosphate, dialkoxypropylphosphates wherein the alkyl groups have linear chains of 12–20 carbon atoms, N-(2,3-di(9-(Z)-octa-decenyloxy))-prop-1-yl-N,N,N-trimethyl-ammonium chloride (DOTMA), as disclosed in U.S. patent application Ser. No. 811,146 filed on Dec. 19, 1985, which is hereby incorporated herein by reference, sphingomyelin, cardiolipin, and the like.

Liposomes utilized in the present invention preferably have a high negative charge density to stabilize the suspension and to prevent spontaneous aggregation.

For use in the present invention the liposomes should be capable of binding to an sbp member and be capable of having a photosensitizer and/or chemiluminescent compound associated with either the aqueous or the nonaqueous phase. The liposomes utilized in the present invention will usually have sbp members bound to the outer surface of the lipid vesicle.

Liposomes may be produced by a variety of methods including hydration and mechanical dispersion of dried phospholipid or phospholipid substitute in an aqueous solution. Liposomes prepared in this manner have a variety of dimensions, compositions and behaviors. One method of reducing the heterogeneity and inconsistency of behavior of mechanically dispersed liposomes is by sonication. Such a method decreases the average liposome size. Alternatively, extrusion is usable as a final step during the production of the liposomes. U.S. Pat. No. 4,529,561 discloses a method of extruding liposomes under pressure through a uniform pore-size membrane to improve size uniformity.

Preparation of liposomes containing a hydrophobic or amphiphilic photosensitizer and/or a chemiluminescent compound dissolved in the lipid bilayer can be carried out in a variety of methods, including a method described by Olsen, et al., *Biochemica et Biophysica Acta*, 557(9), 1979. Briefly, a mixture of lipids containing the appropriate compound(s) in an organic solvent such as chloroform is dried to a thin film on the walls of a glass vessel. The lipid film is hydrated in an appropriate buffer by shaking or vortexing. Thereafter, the lipid suspension is extruded through a series of polycarbonate filter membranes having successively smaller pore sizes. For example, 2.0, 1.0, 0.8, 0.6, 0.4, and 0.2 microns. Repeated filtration through any of the filters, and in particular through the smallest filter, is desirable. The liposomes can be purified by, for example, gel filtration, such as through a column of Sephacryl S-1000. The column can be eluted with buffer and the liposomes collected. Storage in the cold prolongs shelf-life of the liposomes produced by this method. Alternatively the photosensitizer and/or chemiluminescent compound can be added to the liquid suspension following preparation of the liposomes.

Labeling of droplets and liposomes will often involve, for example, inclusion of thiol or maleimide or biotin groups on the molecules comprising the lipid bilayer. Photosensitizers, chemiluminescent molecules and/or sbp members may then be bound to the surface by reaction of the particles with one of these materials that is bound to a sulfhydryl reactive reagent, a sulfhydryl group, or avidin, respectively. Sulfhydryl reactive groups include alkylating reagents such as bromoacetamide and maleimide.

Sbp members can be attracted to the surface of the liposome particles by weak hydrophobic interactions, however such interactions are not generally sufficient to withstand the shear force encountered during incubation and washing. It is preferable to covalently bond sbp members to a liposome particle that has been functionalized, for example by use of DOPE-MCC, as shown above, by combining said liposome with the selected sbp member functionalized with a mercaptan group. For example, if the sbp member is an antibody, it may be reacted with S-acetyl-mercaptosuccinic anhydride (SAMSA) and hydrolyzed to provide a sulfhydryl modified antibody.

Latex particles—"Latex" signifies a particulate water suspendible water insoluble polymeric material usually having particle dimensions of 20 nm to 20 mm, more preferably 100 to 1000 nm in diameter. The latex is frequently a substituted polyethylene such as: polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyrridine, vinyl-chloride acrylate copolymers, and the like. Non-crosslinked polymers of styrene and carboxylated styrene or styrene functionalized with other active groups such as amino, hydroxyl, halo and the like are preferred. Frequently, copolymers of substituted styrenes with dienes such as butadiene will be used.

The association of the photosensitizer and chemiluminescent compound with latex particles utilized in the present invention may involve incorporation during formation of the particles by polymerization but will usually involve incorporation into preformed particles, usually by noncovalent dissolution into the particles. Usually a solution of the chemiluminescent compound and photosensitizer will be employed. Solvents that may be utilized include alcohols, including ethanol, ethylene glycol and benzyl alcohol; amides such as dimethyl formamide, formamide, acetamide and tetramethyl urea and the like; sulfoxides such as dimethyl sulfoxide and sulfolane; and ethers such as carbitol, ethyl carbitol, dimethoxy ethane and the like, and water. The use of solvents having high boiling points in which the particles are insoluble permits the use of elevated temperatures to facilitate dissolution of the compounds into the particles and are particularly suitable. The solvents may be used singly or in combination. Particularly preferred solvents for incorporating photosensitizer are those that will not quench the triplet excited state of the photosensitizer either because of their intrinsic properties or because they can subsequently be removed from the particles by virtue of their ability to be dissolved in a solvent such as water that is insoluble in the particles. Hydroxylic solvents, i.e., those containing one or more hydroxyl groups, are preferred, and generally solvents that will swell but not dissolve the particle can be used. For incorporating chemiluminescent compounds in particles solvents should be selected that do not interfere with the luminescence because of their intrinsic properties or because they can be removed from the particles. Frequently, hydroxylic solvents are also preferred. Typical aromatic cosolvents including dibutylphthalate, benzonitrile, naphthonitrile, dioctylterephthalate, dichlorobenzene, diphenylether, dimethoxybenzene, etc, will be used at sufficiently low concentrations to avoid dissolution of the particles but at sufficient concentrations to swell the particles.

Except when the photosensitizer and/or chemiluminescent compound is to be covalently bound to the particles, it will usually be preferable to use electronically neutral photosensitizers or chemiluminescent compounds. It is preferable that the liquid medium selected does not soften the polymer beads to the point of stickiness. A preferred technique comprises suspending the selected latex particles in a liquid medium in which the photosensitizer and/or chemiluminescent compound has at least limited solubility. Preferably, the concentrations of the photosensitizer and chemiluminescent compound in the liquid media will be selected to provide particles that have the highest efficiency of singlet oxygen formation and highest quantum yield of emission from the chemiluminescent compound in the media but less concentrated solutions will sometimes be preferred. Distortion or dissolution of the particles in the solvent can be prevented by adding a miscible cosolvent in which the particles are insoluble.

Generally, the temperature employed during the procedure will be chosen to maximize the singlet oxygen formation ability of the photosensitizer associated with the particles and the quantum yield of the chemiluminescent compound associated with the particles with the proviso that the particles should not melt or become aggregated at the selected temperature. Elevated temperatures are normally employed. The temperatures for the procedure will generally range from 20° C. to 200° C., more usually from 50° C. to 170° C. It has been observed that some compounds that are nearly insoluble at room temperature, are soluble in, for example, low molecular weight alcohols, such as ethanol and ethylene glycol and the like, at elevated temperatures. Carboxylated modified latex particles have been shown to tolerate low molecular weight alcohols at such temperatures.

An sbp member may be physically adsorbed on the surface of the latex particle or may be covalently bonded to the particle. In cases wherein the sbp member is only weakly bound to the surface of the latex particle, the binding may in certain cases be unable to endure particle-to-particle shear forces encountered during incubation and washings. Therefore, it may be preferable to covalently bond sbp members to the latex particles under conditions that will minimize adsorption. This may be accomplished by chemically activating the surface of the latex. For example, the N-hydroxysuccinimide ester of surface carboxyl groups can be formed and the activated particles to reduce nonspecific binding of assay components to the particle surface, are then contacted with a linker having amino groups that will react with the ester groups or directly with an sbp member that has an amino group. The linker will usually be selected to reduce nonspecific binding of assay components to the particle surface and will preferably provide suitable functionality for both attachment to the latex particle and attachment of the sbp member. Suitable materials include maleimidated aminodextran (MAD), polylysine, aminosaccharides, and the like. MAD can be prepared as described by Hubert, et al., *Proc. Natl. Acad. Sci.*, 75(7), 3143, 1978.

In one method, MAD is first attached to carboxyl containing latex particles using a water soluble carbodiimide, for example, 1-(3-dimethylaminopropyl)-3-ethyl carbodiimide. The coated particles are then equilibrated in reagents to prevent nonspecific binding. Such reagents include proteins such as bovine gamma globulin (BGG), and detergent, such as Tween 20, TRITON X-100 and the like. A sbp member having a sulfhydryl group, or suitably modified to introduce a sulfhydryl group, is then added to a suspension of the particles, whereupon a covalent bond is formed between the sbp member and the MAD on the particles. Any excess unreacted sbp member can then be removed by washing.

Metal sols—are those particles comprised of a heavy metal, i.e., a metal of atomic number greater than 20 such as a Group IB metal, e.g., gold or silver or chalcogens such as selenium or tellurium.

Metal sol particles are described, for example, by Leuvering in U.S. Pat. No. 4,313,734, the disclosure of which is incorporated herein by reference in its entirety. Such sols include colloidal aqueous dispersion of a metal, metal compound, or polymer nuclei coated with a metal or metal compound.

The metal sols may be of metals or metal compounds, such as metal oxides, metal hydroxides and metal salts or of polymer nuclei coated with metals or metal compounds. Examples of such metals are platinum, gold, silver, mercury, lead, palladium, and copper, and of such metal compounds are silver iodide, silver bromide, copper hydrous oxide, iron oxide, iron hydroxide or hydrous oxide, aluminum hydroxide or hydrous oxide, chromium dioxide or hydrous oxide, vanadium oxide, arsenic sulphide, manganese hydroxide, lead sulphide, mercury sulphide, barium sulphate and titanium dioxide. In general, the metals or metal compounds useful may be readily demonstrated by means of known techniques.

It is sometimes advantageous to use sols comprised of dispersed particles consisting of polymer nuclei coated with the above mentioned metals or metal compounds. These particles have similar properties as the dispersed phase of pure metals or metal compounds, but size, density and metal contact can be optimally combined.

The metal sol particles may be prepared in a large number of ways which are in themselves known. For example, for the preparation of a gold sol Leuvering refers to an article by G. Frens in *Nature Physical Science* 241, 20 (1973).

The metal sol particles can be modified to contain various functional groups as described above for linking to an sbp member, a photosensitizer and a chemiluminescent compound. For example, polymeric bonding agents can be used to coat the particles such as polymers containing thiol groups that bond strongly to many heavy metals or silylating agents that can bond and form polymeric coatings as, for example, by reaction of metal particles with trialkoxy aminoalkylsilanes as described in EPO Patent Appl. 84400952.2 by Advanced Magnetics for coating magnetic particles.

Dye crystallites—microcrystals of pure or mixed solid water insoluble dyes, preferably dyes that can serve as the photosensitizers described above. The dye crystallites useful in the present invention have a size range of 20 nm to 20 mm.

One method for preparing dye crystallites is described in U.S. Pat. No. 4,373,932 (Gribnau, et al.), the disclosure of which is incorporated herein by reference in its entirety. Gribnau describes colloidal dye particles and aqueous dispersions of a hydrophobic dye or pigment, which may have an immunochemically reactive component and a chemiluminescent compound directly or indirectly attached. The dye particles are prepared in general by dispersing a dye in water and then centrifuging. A dye pellet is obtained and resuspended in water, to which glass beads are added. This suspension is rolled for several days at room temperature. The liquid is decanted and centrifuged, and the dye particles are obtained after aspiration of the liquid.

Another method for preparing dye crystallites is by slow addition of a solution of the dye in a water miscible solvent to water. Another method is by sonication of a suspension of the solid dye in water.

Binding of sbp members to the dye particles can be achieved by direct or indirect adsorption or covalent chemical attachment. The latter can also be used for attachment of a chemiluminescent compound and is governed by the presence of suitable functional groups in any coating material and in the dye. For example, functional groups can be introduced onto the surface of a dye crystallite by coupling a compound containing a diazotized aromatic amino group and the desired functional group to a phenolic or anilino group of the dye.

Where the dye has a carboxyl group, the dye crystallite can be activated by a carbodiimide and coupled to a primary amino component. Aliphatic primary amino groups and hydroxyl groups can be activated, for example, by cyanogen bromide or halogen-substituted di- or tri-azines, after which attachment with a primary amino component or with, for example, a component containing a —SH, or —OH or group can take place. Use can also be made of bifunctional reactive compounds. For example, glutaraldehyde can be used for the mutual coupling of primary amino components of the dye and an sbp member, and, for example, a hetero-bifunctional reagent such as N-succinimidyl 3-(2-pyridyldithio) propionate can be employed for the coupling of a primary amino component to a component containing a thiol group.

Emulsions of the present invention can be prepared as follows. Metal sols can be prepared by reductive precipitation, for example, by the action of hydrazine on silver nitrate solutions. Oils can be emulsified by sonication of aqueous oil suspensions and/or by extrusion through microporous filters. Oil emulsions can also be obtained by dilution of a solution of an oil in a water miscible solvent such as methanol into water. Stable emulsions form only when there are surfactants present in the water such as anionic detergents, proteins, phospholipids and the like.

Chemiluminescent compound (CC)—a photoactivatable substance that undergoes a chemical reaction upon direct or sensitized excitation by light or upon reaction with singlet oxygen to form a metastable reaction product that is capable of decomposition with the simultaneous or subsequent emission of light, usually within the wavelength range of 250 to 1200 nm. The term "photoactivatable" includes "photochemically activatable". CC's that are preferred in the present invention are those that react with singlet oxygen to form dioxetanes or dioxetanones. The latter are usually electron rich olefins (1). Exemplary of such electron rich olefins are enol ethers, enamines, 9-alkylidene-N-alkylacridans, arylvinylethers, dioxenes, arylimidazoles, 9-alkylidene-xanthanes and lucigenin. Other compounds that are included in the term "CC" include luminol and other phthalhydrazides and chemiluminescent compounds that are protected from undergoing a chemiluminescent reaction by virtue of their being protected by a photochemically labile protecting group, such compounds including, for example, firefly luciferin, aquaphorin, luminol, etc.

The CC's of interest will preferably emit at a wavelength above 300 nanometers, preferably above 500 nanometers, and more preferably above 550 nm. Compounds that absorb and emit light at wavelengths beyond the region where the sample components contribute significantly to light absorption will be of particular use in the present invention. The absorbance of serum drops off rapidly above 500 nm and becomes insignificant above 600 nm; therefore, chemiluminescent compounds that emit light above 600 nm are of particular interest. However, chemiluminescent compounds that absorb at shorter wavelengths are useful when interference absorbance of the sample is absent.

In order to avoid autosensitization of the chemiluminescent compound, it is preferable that the chemiluminescent compounds do not absorb light used to excite the photosensitizer. Since it will generally be preferable to excite the sensitizer with light wavelengths longer than 500 nm, it will therefore be desirable that light absorption by the chemiluminescent compound be very low above 500 nm.

Where long wave length emission from the chemiluminescent compound is desired, a long wavelength emitter such as a pyrene, bound to the chemiluminescent compound can be used. Alternatively, a fluorescent molecule can be included in the medium containing the chemiluminescent compound. Preferred fluorescent molecules will be excited by the activated chemiluminescent compound and emit at a wavelength longer than the emission wavelength of the chemiluminescent compound, usually greater that 550 nm. It is usually also desirable that the fluorescent molecules do not absorb at the wavelengths of light used to activate the photosensitizer. Examples of useful dyes include rhodamine, ethidium, dansyl, Eu(fod)$_3$, Eu(TTA)$_3$, Ru(bpy)$_3^{++}$ (wherein bpy=2,2'-dipyridyl, etc. In general these dyes act as acceptors in energy transfer processes and preferably have high fluorescent quantum yields and do not react rapidly with singlet oxygen. They can be incorporated into particles simultaneously with the incorporation of the chemiluminescent compound into the particles. The CC's 1 below generally do not contain chemically reactive allylic CH or NH groups.

The electron rich olefins 1 generally have an electron donating group in conjugation with the olefin:

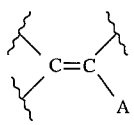
(1)

wherein A is an electron donating group such as, for example, N(D)$_2$, OD, p-C$_6$H$_4$N(D)$_2$, furanyl, N-alkylimidazole, N-alkylpyrrolyl, 2-indoyl, etc., wherein D is, for example, alkyl or aryl, and A is either bound directly to the olefinic carbon or bound by the intermediacy of other conjugated double bonds. The other valencies of the C atoms in olefin 1 are substitutents of 1 to 50 atoms, which may be taken together to form one or more rings, which are fused or unfused, e.g., cycloalkyl, phenyl, 7-norbornyl, naphthyl, anthracyl, acridanyl, adamantyl, and so forth.

Usually there will be no atom bearing a hydrogen atom that is directly attached to the olefin unless that atom is at a position which cannot accommodate a double bond such as at a bridgehead position of a small bicyclic ring system. The more preferred olefins are those that yield a dioxetane that decays rapidly at room temperature (less than 60 minutes, preferably less than 5 minutes, desirably less than 30 sec). The dioxetanes may be luminescent alone or in conjunction with a fluorescent energy acceptor.

Enol ethers 2 generally have the structure:

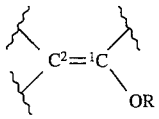
(2)

wherein R is alkyl of 1 to 20 carbon atoms and the remaining substituents on the olefin are selected from the group consisting of H and substituents of 1 to 50 atoms, preferably. Useful enol ether compounds are those with an aryl on the same carbon as the ether where the aryl ring is substituted with an electron donating group at a position that imparts fluorescence. The electron donating group can be, for example, m-hydroxyphenyl, m-dimethylamino-phenyl, 1-(5-aminonaphthyl), pyryl, 1-(3-hydroxypyryl), anthracyl, chrysyl, etc. One or both groups at the 2-position can be aryl where the ketone formed by replacing the 1-carbon with oxygen is fluorescent, for example, β-naphthyl, or 2-anthryl. Exemplary enol ethers by way of illustration and not limitation are:

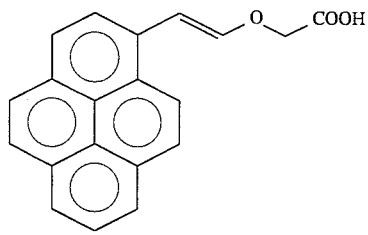
(3)

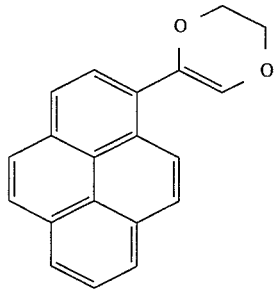
(4)

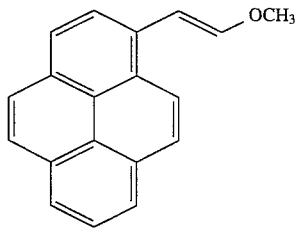
(5)

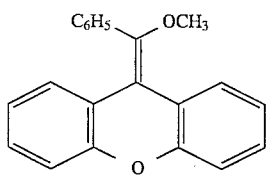
(6)

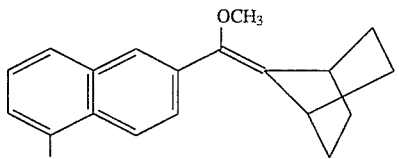
(7)

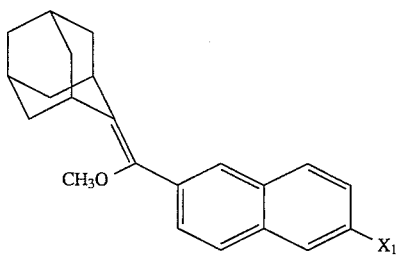
(8)

wherein X$_1$ is H, OC(O)CH$_3$, OCH$_3$, OH, described by Bronstein, et al., in U.S. Pat. No. 4,956,477;

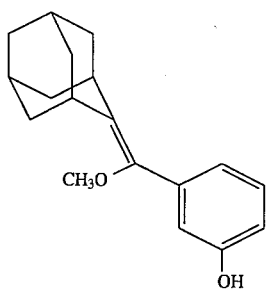
(9)

described by Bronstein, et al., in U.S. Pat. No. 4,956,477;

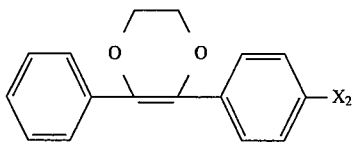
(10)

wherein $X_2$ is H, OH, $N(CH_3)_2$ or $OCH_3$, described by P. Schaap, *J. Am, Chem. Soc.*, 104: 3504 (1982) and P. Schaap, *Photochem. and Photobiology* 30:35 (1979);

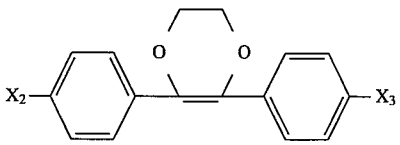
(11)

wherein $X_2$ is defined above, $X_3$ is H, $OCH_3$, or $N(CH_3)_2$, described by P. Schaap, Report to U.S. Army Research Office, Oct. 15, 1986, and S.D. Gagnon, Ph.D. Thesis, Wayne State University (1982);

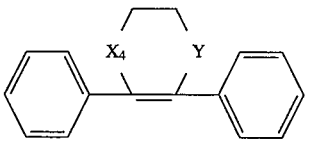
(12)

wherein $X_4$=O, S, $CH_3N$, or PhN and Y=O, S, or $CH_3N$ and Ph=phenyl, described by P. Schaap, *Report to office of Naval Research*, Mar. 17, 1987;

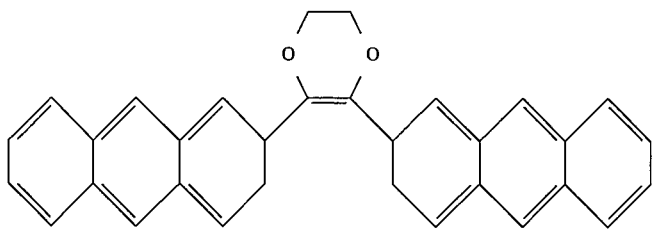
(13)

described by P. Schaap, Report to U.S. Army Research, Oct. 15, 1986;

Enamines 7 generally have the structure:

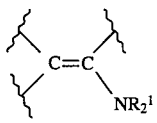
(14)

wherein $R^1$ is independently aryl or alkyl and the remaining substituents on the olefin are selected from the group consisting of H and substituents of 1 to 50 atoms. In general, useful enamines will be governed by the rules set forth above for enol ethers.

Examples of useful enamines, by way of example and not limitation, are the above enol ethers 3–5 with $N(CH_3)_2$ in place of $OCH_3$. A further example is

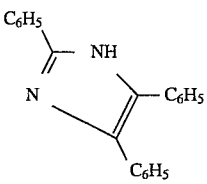
(15)

9-Alkylidene-N-alkylacridans 10 generally have the structure:

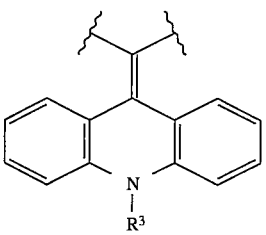
(16)

wherein $R^3$ is alkyl and the remaining substituents on the olefin are selected from the group consisting of H and substituents of 1 to 50 atoms, preferably, phenyl, naphthyl, phenanthryl, m-methoxyphenyl, dimethylamino, trityl, methoxy, N-morpholeno and may be taken together to form a ring such as, for example, adamantyl, N-methyacridanylide, xanthanylidine, 1-(3,4-benzo-5-hydrofurylidene), and the like.

Particular examples of 9-alkylidine-N-alkylacridans useful as labels in the present invention are, by way of illustration and not limitation:

(17)

described by Singer, *J. Org. Chem.* 41, 2685, (1976);

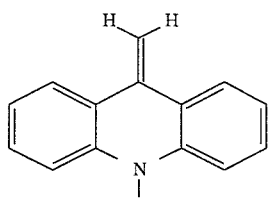

described by E. White, *Chem, Letters;* 1491 (1979);

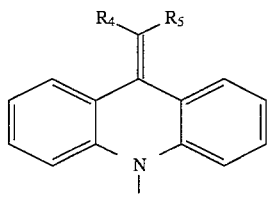

wherein $R_4$ and $R_5$ are independently H or phenyl, described by Singer, et al., *J. Am. Chem. Soc.* 102: 3823, (1983);

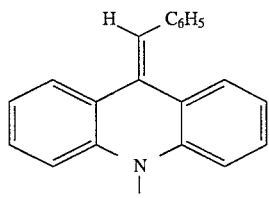

described by McCapra, *Chem. Comm;* 944 (1977) and Singer, et. al., ibid;

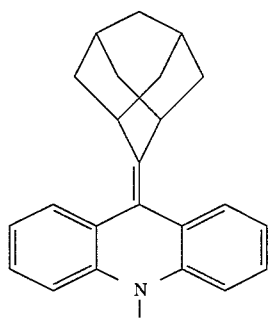

described by McCapra, ibid;

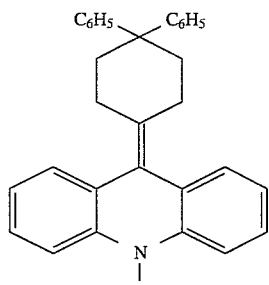

described by McCapra, ibid;

The relevant portions of the above references are incorporated herein by reference.

9-Alkylidene-xanthanes generally have the structure:

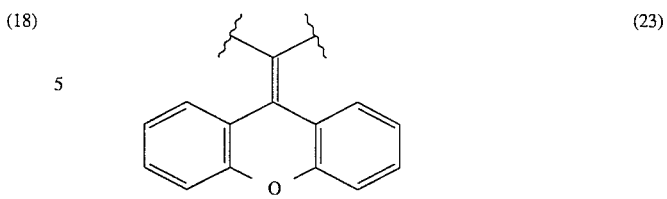

where the substituents on the olefin are selected from the group consisting of H and substituents of 1 to 50 atoms, preferably, phenyl, naphthyl, phenanthryl, m-methoxyphenyl, dimethylamino, trityl, methoxy, N-morpholeno and may be taken together to form a ring such as, for example, adamantyl, N-methyacridanylide, xanthanylidine, 1-(3,4-benzo-5-hydrofurylidene), and the like, for example, 9-phenyl-methylidene-xanthene.

Another family of CC's is 2,3-dihydro-1,4-phthalazinediones. The most popular compound is luminol, which is the 5-amino compound. Other members of the family include the 5-amino-6,7,8-trimethoxy and the dimethylamino[ca] benz analog. It should be noted that luminol has been used as a label in assays; however, excitation of the luminol has been accomplished chemically, not by photoactivation as is the case in the present invention. These compounds are oxidized to the 1,4-phthalazinidiones by singlet oxygen and under subsequent reaction with superoxide or hydrogen peroxide undergo decomposition with light emission.

Another family of CC's is the 2,4,5-triphenylimidazoles, with lophine as the common name for the parent product. Chemiluminescent analogs include para-dimethylamino and -methoxy substituents.

Other chemiluminescent compounds that satisfy the requirements given above may be found in European Patent Application No. 0,345,776.

Dioxetanes formed by the reaction of singlet oxygen with the chemiluminescent compound have the general structure below where the substituents on the carbon (C) atoms are those present on the corresponding olefin:

Some of the dioxetanes decompose spontaneously, others by heating, with the emission of light. In some cases the dioxetane is spontaneously converted to a hydroperoxide whereupon base is required to reform the dioxetane and permit decomposition and light emission.

Energy acceptor—referred to herein also as fluorescent energy acceptor. A chromophore having substantial absorption higher than 310 nm, normally higher than 350 nm, and preferably higher than about 400 nm. The choice of the energy acceptor will also be governed by the particular CC. The energy acceptor should be capable of absorbing light emitted by the CC. Preferably, the absorption maximum of the energy acceptor should be at similar wavelength as the emission maximum of the chemiluminescent compound. A high extinction coefficient is desirable, usually in excess of 10, preferably in excess of $10^3$, and particularly preferred in excess of $10^4$. The energy acceptor must be fluorescent and will preferably have a high fluorescence quantum yield, usually at least 0.1, preferably greater than 0.4.

A number of different molecules useful as the energy acceptor are described by Ullman, et al. I, II, IV and V, at columns 8 and 9, the relevant portions of which are incorporated herein by reference.

One group of fluorescers having a number of the desirable properties described above are the xanthene dyes, which include the fluoresceins derived from 3,6-dihydroxy-9-phenyl-xanthhydrol and rosamines and rhodamines, derived from 3,6-diamino-9-phenylxanthhydrol. The rhodamines and fluoresceins have a 9-o-carboxyphenyl group, and are derivatives of 9-o-carboxyphenyl- xanthhydrol.

These compounds are commercially available with substituents on the phenyl group which can be used as the site for bonding or as the bonding functionality. For example, amino and isothiocyanate substituted fluorescein compounds are available.

Another group of fluorescent compounds are the naphthylamines, having an amino group in the alpha or beta position, usually alpha position. Included among the naphthylamino compounds are 1-dimethylaminonaphthyl-5-sulfonate, 1-anilino-8-naphthalene sulfonate and 2-p-toluidinyl-6-naphthalene sulfonate.

Dye precursors that are activated to react with proteins include 3-phenyl-7-isocyanatocoumarin; acridines such as 9-isothiocyanatoacridine; N-(p-(2-benzoxazolyl)phenyl) maleimide; benzoxadiazoles

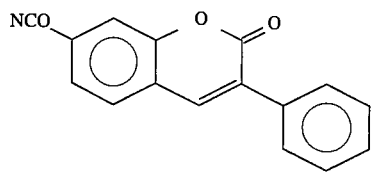
(28)

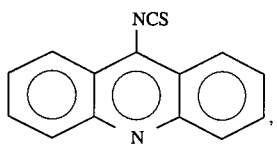
(29)

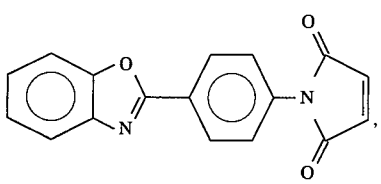
(30)

and

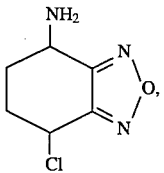
(31)

such as 4-chloro-7-nitrobenzo-2-oxa-1,3-diazole; stilbenes, such as 4-dimethylamino-4'-isothiocyanatostilbene and 4-dimethylamino 4'-maleimidostilbene. Other dyes that an be further functionalized to combine with an sbp member include acridine orange, 7-(p-methoxybenzylamino)-4-nitrobenzo-2-oxa-1,3-diazole; N,N'-dioctadecyloxacarbocyanine p-toluenesulfonate; pyrenes, such as 8-hydroxy-1,3,6-pyrenetrisulfonic acid, and 1-pyrenebutyric acid, merocyanine 540, rose bengal, as well as other readily available fluorescing molecules.

For polynucleotide assays a large variety of energy acceptors can be used, but those that have enhanced fluorescence when bound to double stranded nucleic acids are preferred. Dyes that intercalate such as ethidium bromide and acridine orange are typical examples. A ruthenium derivative developed by Barton (*J. Am. Chem. Soc.* (1990) 112:4960) is particularly attractive because it is dramatically switched on when intercalated. Alternatively, the energy acceptor may be bound to a second polynucleotide probe that can bind near to the chemiluminescent compound labeled probe or the energy acceptor may be unbound and freely dispersed in solution.

The photosensitizer and the CC are both associated with a particle to form the matrix of the present invention. The matrix is associated with an sbp member. This may be accomplished in a number of ways, as described above. For example, the photosensitizer or the CC or the particle may contain a functionality for attachment to an sbp member or the sbp member may contain the functionality for attaching to the photosensitizer, the CC or the particle. The attachment may be accomplished by a direct bond between molecules or a linking group can be employed between the sbp member and the photosensitizer, the CC or the particle. In another embodiment the photosensitizer and the CC can be bound to or incorporated in a particle, to which is also attached an sbp member. The sbp member can be capable of binding to the analyte. The photosensitizer and CC can be incorporated into the particle by virtue of being soluble in at least one phase of the particle. The photosensitizer or CC may be bound to the particle when it is not incorporated into the particle. For this purpose the photosensitizer or CC or the particle, or component thereof, is functionalized to provide a means of attaching the photosensitizer and/or the CC to the particle. For particles that are oil droplets or lipid bilayers, the photosensitizer and/or the CC can be bound to the particle by attachment to a long hydrocarbon chain that is compatible with the particle composition. Frequently, at least one, and preferably two, hydrocarbon chains are employed having 8 to 20 or more carbon atoms.

If the particle is a droplet of a fluorocarbon, the photosensitizer and/or the CC may be fluorinated to enhance solubility and reduce exchange and the hydrocarbon chain used for linking will preferably be replaced with a fluorocarbon chain. For silicon particles the photosensitizer and/or the CC may be bound to a polysiloxane. Usually, it will be desirable to minimize the charge and polarity of the photosensitizer and the CC so that in this approach they will reside within the non-aqueous portion of the particle. Binding of photosensitizer to an sbp member is described fully in the Application.

As mentioned above, the photosensitizer and chemiluminescent compound can be incorporated into particles by virtue of being soluble in at least one phase of the particles, in which case the photosensitizer and chemiluminescent compound will be at much higher concentration within the particle than in the bulk assay medium. When the photosensitizer and chemiluminescent compound are covalently bound to particles, the photosensitizer and chemiluminescent compound or the particles, or components thereof, are functionalized to provide a means of attaching the photosensitizer and chemiluminescent compounds and the particles. For particles that are oil droplets or liposomes the photosensitizer and chemiluminescent compound can be attached to one or more long hydrocarbon chains, each generally having at least 10 to 30 carbon atoms. If the particles are droplets of a fluorocarbon, the photosensitizer or chemiluminescent compound incorporated into these particles may be fluorinated to enhance solubility and reduce exchange into other particles bound with the other label, and the hydrocarbon chain used for linking will preferably be replaced with a fluorocarbon chain. For silicon fluid particles the photosensitizer and chemiluminescent compound can be bound to a polysiloxane. In order to maximize the number of photosensitizer and chemiluminescent compound molecules per particle, it will usually be desirable to minimize the charge and polarity of the photosensitizer and chemiluminescent compound so that it resides within the non-aqueous portion of the particle. When the particle is a liposome and it is desired to retain the photosensitizer and chemiluminescent compound in the aqueous phase of the liposome, it will be preferred to use photosensitizers and chemiluminescent compounds that are highly polar or charged.

The following is, by way of illustration and not limitation, a typical preparation for polystyrene particles in accordance with the present invention. Polystyrene particles (175 nm) are prepared by heating in the presence of a mixture of both photosensitizer and CC. The medium employed is a mixture of water, ethylene glycol, and benzyl alcohol in the approximate ratio of 1:8:1 by volume. This mixture provides a balance of both aqueous and organic properties. A water-like solvent is preferred to maintain the colloidal stability of the beads while an organic-like solvent is preferred to solubilize the dyes. Other solvent mixtures can be used as the medium; however, the above medium is generally acceptable for a variety of particle preparations in accordance with the present invention.

Photosensitizer and CC are separately prepared as solutions (5 mM) in benzyl alcohol. Aliquots in varying ratios are then added to a mixture of ethylene glycol, benzyl alcohol 9:1 by volume and the mixture heated to 100° to 110°. Appropriate aliquots of the particles, into which the photosensitizer and the CC are to be incorporated, are then added to the hot mixture while stirring vigorously. Heating is continued briefly and then the mixture is cooled and diluted with ethanol. Excess dye and solvent mixture are removed by repeated centrifugation. Finally, the washed particles are resuspended in a convenient volume of water (generally 100 mg per 1 to 10 ml water) and stored in the dark.

The photosensitizer, the CC and the sbp member are "associated with" a particle to form the matrix of the present invention. As used herein, the term "associated with" includes the following: The association may be through covalent or non-covalent binding or, as with the photosensitizer and the CC, through incorporation into a particle. In general, a suspendible particle in which the photosensitizer and the CC are incorporated will have the sbp member bound to it. This sbp member is generally capable of binding to the analyte or to an sbp member capable of binding to the analyte. When another sbp member is utilized and is also capable of binding to the analyte, a sandwich assay protocol results. The sbp member of the matrix can also be analogous to the analyte, in which case a competitive assay protocol can result.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, polyanions such as dextran sulfate; surfactants, particularly non-ionic surfactants; binding enhancers, e.g., polyalkylene glycols; or the like.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

The invention has particular application in the diagnostic assay area. A combination is provided comprising (1) a medium suspected of containing an analyte and (2) a label reagent comprising a first specific binding pair (sbp) member associated with a single composition having both a photosensitizer and a CC. Conditions are chosen such that an sbp member complex is formed in relation to the presence of the analyte. For example, the first sbp member may be capable of binding to the analyte or a second sbp member to form a complex related to the presence of the analyte. The method further comprises photoactivating the photosensitizer and detecting the amount of luminescence generated by the CC. The amount of luminescence is related to the amount of analyte in the medium.

Generally, the photosensitizer is activated by irradiation with light and, upon irradiation, causes molecular oxygen to be converted to singlet oxygen. The singlet oxygen then activates the CC. The product formed by the activation of the CC with singlet oxygen preferably decomposes spontaneously with emission of light usually with a lifetime of 10 microseconds to 10 hours, preferably 100 microseconds to two hours, nonpreferably, 1 second to 10 minutes.

One of the factors that allow control of the time to luminescence is the structure of the CC. Structural features that contribute to a delay in luminescence are complex and only partially predictable. Schaap, supra, and McCapra, supra, discuss some of the principles involved and the relevant portions of these references are incorporated herein by reference.

Another factor that allows for control of the time to luminescence is the composition or the particle. In general, when the particle is composed of a non-polar material in which the CC is dissolved decay times and quantum efficiencies are increased relation to polar materials.

Another factor that may be used to control the time to luminescence is temperature. In general, increasing the temperature will decrease the decay time.

Another factor in the control of the time to luminescence is the presence of activators that enhance the rate of decomposition of the dioxetanes produced in the reaction. Such activators include polarizable solvents such as halocarbons and certain metal chelates such as europium chelates. The activator is usually present in an amount sufficient to achieve the desired delay in time to luminescence. This amount depends on the nature of the activator and generally is about $10^{-5}$ to $10^{-1}$ M.

The photosensitizer serves to activate the CC when the medium containing the above reactants is irradiated. The matrix is irradiated with light having a wavelength of sufficient energy to convert the photosensitizer to an excited state and render it capable of activating molecular oxygen to singlet oxygen. The photosensitizer concentration of the matrix will usually be optimized to give the maximum yield of singlet oxygen and will often be from $10^{-4}$ to $10^{-1}$ M.

The excited state of the photosensitizer will usually be the lowest triplet state and is at least 20 Kcal/mole, preferably at least 23 Kcal/mole, more energetic than the ground state. Generally, the matrix is irradiated with light having a wavelength of about 300 to 1200 nm usually 450 to 950, preferably 550 to 800 nm. The period of irradiation will depend on the lifetime of the activated CC, the light intensity and the desired emission intensity. For short-lived activated CC's the period may be less than a second, usually about a millisecond but may be as short as a microsecond where an intense flashlamp or laser is used. For longer-lived activated CC's the irradiation period can be longer and a less intense steady light source can be used. In general, the integrated light intensity over the period of irradiation should be sufficient to excite at least 0.1% of the photosensitizer molecules, preferably at least 30%, and most preferably every, photosensitizer molecule will be excited at least once.

The luminescence or light produced in any of the above approaches can be measured visually, photographically, actinometrically, spectrophotometrically or by any other convenient means to determine the amount thereof, which is related to the amount of analyte in the medium.

A helium-neon laser is an inexpensive light source for excitation at 632.6 nm. Photosensitizers that absorb light at this wavelength are compatible with the emission line of a helium-neon laser and are, therefore, particularly useful in the present invention. Other light sources include, for example, other lasers such as Argon, YAG, He/Cd, and ruby; photodiodes; mercury, sodium and xenon vapor lamps; incandescent lamps such as tungsten and tungsten/halogen; and flashlamps.

One particular application of the methods and compositions of the invention is a method for determining an analyte. The method comprises the steps of subjecting a medium suspected of containing an analyte to conditions under which a complex of sbp members is formed in relation to the presence of the analyte and determining whether the sbp member complex has formed. A particulate composition of the invention is employed as a label to assist in the determination. An sbp member complex involving the label reagent is formed in relation to the presence of analyte in the medium. The composition is then irradiated with light and light energy from the chemiluminescent compound is measured such as, for example, by visual inspection, by instrument or by use of a fluorescent energy acceptor, the presence or intensity thereof being related to the amount of analyte in the medium.

Another aspect of the present invention is a composition comprising a solid matrix having incorporated therein a photosensitizer capable upon activation of generating singlet oxygen and a chemiluminescent compound capable of being activated by singlet oxygen. The photosensitizer can be covalently bound to the chemiluminescent compound but is usually not bound. One or both the photosensitizer and the chemiluminescent compound can be covalently linked to the matrix or can be associated with the matrix with no covalent bounds. The composition can comprise one or a plurality of distinct chemiluminescent compounds and one or a plurality of distinct photosensitizers and can further be comprised of one or a plurality of fluorescent compounds capable of gathering light energy and transferring it to the photosensitizer or accepting energy from the chemiluminescent compound. The distinct chemiluminescent compounds may differ by differing rates of activation by singlet oxygen. The composition may also comprise an activator that may or may not be fluorescent and that enhances the decay of an activated chemiluminescent compound. The composition can further comprise a member of a specific binding pair (sbp) bound thereto wherein the composition is usually particulate.

Another aspect of the present invention is a composition comprising a particle having incorporated therein a photosensitizer capable of generating singlet oxygen and a chemiluminescent compound capable of being activated by singlet oxygen, where the particle is bound to a molecule useful in the detection of an analyte. The molecule is a member of a specific binding pair.

The photosensitizer can be covalently bound to the chemiluminescent compound but normally is noncovalently associated with the CC in the particle. The photosensitizer and the chemiluminescent compound may be dissolved in the particle.

The method and compositions of the invention may be adapted to most assays involving sbp members such as ligand-receptor, e.g., antigen-antibody reactions, polynucleotide binding assays, and so forth. The assays are usually heterogeneous, including competitive and sandwich, but may be homogeneous particularly where an energy acceptor is utilized.

The ability of luminescence produced by an activated CC to activate a fluorescent energy acceptor may be governed by the binding of the two sbp members or may be the consequence of a relatively high concentration of the energy acceptor in the matrix containing the activated CC, wherein the concentration will usually be at least micromolar, usually at least millimolar. When activation is governed by binding, the initial concentration of the energy acceptor in the assay medium will be quite low, often $10^{-15}$ to $10^{-6}$ M, usually $10^{-12}$ to $10^{-8}$ M.

In a heterogeneous assay approach, a sample suspected of containing an analyte, which is an sbp member, is combined with a particulate matrix of the present invention that is comprised of a complementary sbp member. The matrix is then separated from the liquid phase and either the solid phase or the liquid phase is examined for the presence of luminescent energy, usually by irradiating the particular phase in question and measuring the amount of light emitted. Alternatively, the assay can be carried out in a homogeneous mode where a separation step is not employed. In this situation an energy acceptor associated with another sbp member is employed wherein the sbp member is either complementary to (sandwich) or analogous to (competitive) the analyte. The energy acceptor is frequently incorporated into a particle to which the sbp member is bound. These materials are generally combined either simultaneously or wholly or partially sequentially. The binding of the sbp members occurs in relation to the amount of analyte present and results in the energy acceptor being brought into close proximity to the activated CC and able to accept the energy emitted. Comparison of values obtained in the test run with those obtained using controls of known concentration enable the determination of the presence or and amount of the analyte.

In a specific binding assay, the sample may be pretreated, if necessary, to remove unwanted materials. The immunological reaction for a sandwich type assay usually involves an sbp member, e.g., an antibody, that is complementary to the analyte and bound to the particulate matrix, a second sbp member, e.g., antibody, that is also complementary to the analyte, and the sample of interest. The immunological reaction for a competitive protocol usually involves an sbp member that is complementary to the analyte and an sbp member that is analogous to, usually a derivative of, the analyte. One of these sbp members will be associated with the particulate matrix.

An assay for the analyte will normally be carried out in an aqueous buffered medium at a moderate pH, generally that which provides optimum assay sensitivity. As explained above, the assay is usually performed with separation (heterogeneous) of bound and unbound fractions of the particulate matrix.

The aqueous medium may be solely water or may include from 0.01 to 80 or more volume percent of a cosolvent. The pH for the medium will usually be in the range of about 4 to 13, more usually in the range of about 5 to 10, and preferably in the range of about 6.5 to 9.5. The pH will usually be a compromise between optimum binding of the binding members and the pH optimum for minimizing non-specific binding and maximizing quantum efficiency. For example, the activated CC may require a certain pH range in order to decay to produce luminescence.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred.

Moderate temperatures are normally employed for carrying out the assay and usually constant temperature, preferably, room temperature, during the period of the measurement. Incubation temperatures will normally range from about 5° to 99° C., usually from about 15° to 70° C., more usually 20° to 45° C. Temperatures during measurements will generally range from about 10° to 70° C., more usually from about 20° to 45° C., more usually 20° to 25° C. In some instances the activated CC may require heating up to 100° C. in order to decay to produce luminescence.

The concentration of analyte which may be assayed will generally vary from about $10^{-5}$ to $10^{-17}$ M, more usually from about $10^{-6}$ to $10^{-14}$ M. Considerations, such as whether the assay is qualitative, semiquantitative or quantitative, the particular detection technique and the concentration of the analyte of interest will normally determine the concentrations of the various reagents.

While the concentrations of the various reagents in the assay medium will generally be determined by the concentration range of interest of the analyte, the final concentration of each of the reagents will normally be determined empirically to optimize the sensitivity of the assay over the range. That is, a variation in concentration of the analyte which is of significance should provide an accurately measurable signal difference.

While the order of addition may be varied widely, there will be certain preferences depending on the nature of the assay. The simplest order of addition is to add all the materials simultaneously. Alternatively, the reagents can be combined wholly or partially sequentially. Optionally, an incubation step may be involved after the reagents are combined, generally ranging from about 30 seconds to 6 hours, more usually from about 2 minutes to 1 hour.

In a heterogeneous assay after all of the reagents have been combined, they can be incubated, if desired. Then, the solid and liquid phases are separated and one of the phases is irradiated and the resulting light emitted is measured. The emitted light is related to the amount of the analyte in the sample tested. The amounts of the reagents of the invention employed in a heterogeneous assay depend on the nature of the analyte.

The following compositions and assays are provided by way of illustration and not limitation to enable one skilled in the art to appreciate the scope of the present invention and to practice the invention without undue experimentation. It will be appreciated that the choice of analytes, photosensitizers, CC's, surfaces, particles and reaction conditions will be suggested to those skilled in the art in view of the disclosure herein and the examples that follow.

In the following assays, components are combined in a predominantly aqueous medium of pH 6 to 8.5.

In one embodiment of the invention the chemiluminescent compound 9-benzal-10-methylacridan, is covalently linked to an antibody for thyroid stimulating hormone (TSH). The 9-benzal-10- methylacridan, functionalized with a N-hydroxysuccinimidyl ester of a carboxyl group attached to the phenyl ring, reacts with the amino groups of the antibody. The linking group is a carboxamide. The photosensitizer utilized is rose bengal. The photosensitizer and the chemiluminescent compound bound to antibody are covalently bound to latex particles having an average dimension of 0.5 micron to give Reagent 1. The latex particles and rose bengal and chemiluminescent compound are covalently bound to each other by means of chloromethyl groups on the latex. Covalent binding of rose bengal to chloromethylated latex to provide an ester linking group is described in *J. Am, Chem. Soc.*, 97:3741 (1975). A second antibody for TSH is absorbed onto a microtiter plate well (Reagent 2). Both of the antibodies employed are monoclonal antibodies prepared by standard hybrid cell line technology. One antibody recognizes the α-subunit of TSH and the other recognizes the β-subunit of TSH. In conducting the assay a serum sample suspected of containing TSH is obtained from a patient.

Fifty microliters of the sample is combined in a 500 mL aqueous medium, buffered with Tris buffer at pH 8.0, with Reagent 1 above. The amount of Reagent 1 is sufficient to provide a concentration of antibody of about $10^{-8}$ molar. The reaction mixture is then added to the microtiter plate well (Reagent 2) and incubated for a period of one hour at 25° C. The reaction mixture is then removed from the well and the plate is washed with a buffered aqueous medium at pH 8.0 and then irradiated for 30 seconds with 560 nm light. The light intensity emitted following the irradiation is measured and the total light energy detected over a period of 30 seconds is compared with values obtained in a similar procedure with samples having known concentrations of TSH to determine the concentration of TSH in the unknown. Alternatively, following incubation and removal from the well, the reaction mixture containing unbound latex particles is similarly irradiated, and the amount of light emitted from the system is measured and compared with control values as before.

In another alternative approach the same Reagent 1 is used. Reagent 2 is a carbon particle (an energy acceptor) to which the second antibody is bound noncovalently. The assay is conducted by mixing 50 microliters of sample, 50 μL of a suspension of Reagent 1, 50 μL of a suspension of Reagent 2 and 500 μL of pH 8.0 Tris buffer, incubating for one hour and irradiating with light. The presence of the analyte is indicated by a reduction in light emission when compared to controls due to the carbon particle being brought into close proximity to the activated chemiluminescent compound by virtue of the presence of TSH in the sample.

In another embodiment in accordance with the present invention, oil droplets (Reagent 3) are prepared from a solution of the photosensitizer, chlorophyll, in mineral oil in accordance with Giaever, supra. The oil droplets, which range from 0.1 to 2 microns in diameter, are functionalized and linked to a monoclonal antibody for human chronic gonadotropin (hCG). The chlorophyll is lipophilic and is therefore dissolved irreversibly in the lipophilic oil droplet. 9-(Diphenylmethylidine)-N methylacridan is also irreversibly dissolved in the lipophilic oil droplets by including a N,N-didodecylcarboxamide group bound to one of the phenyl groups of the acridan. A second monoclonal antibody for hCG, which recognizes a different portion of the hCG molecule than that recognized by the first monoclonal antibody referred to above is adsorbed onto the surface of a microtiter plate. The monoclonal antibodies are prepared by standard hybrid cell line technology. A urine sample suspected of containing hCG (50 microliters) is combined with excess quantities of Reagent 3 in an aqueous buffered medium (500 mL) at pH 7.5 and then placed into the well of the microtiter plate. The medium is incubated at 25° C. for a period of 20 minutes. The medium is then separated from the plate and the plate is washed with buffer at pH 8. The plate is irradiated at >650 nm using a tungsten/halogen lamp with a cut-off filter for a period of one minute and the light emitted is measured as described above. The amount of light is compared with the amount emitted following the above procedure using samples containing known amounts of hCG and the amount of hCG in the unknown sample is determined by comparing the values. In this way a convenient and sensitive immunoassay for hCG is conducted. By including

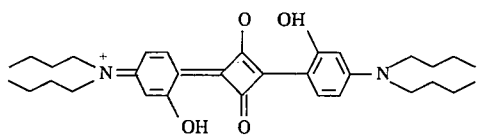

(32)

(prepared as described in U.S. Pat. No. 5,039,818, which is incorporated herein by reference) together with the chlorophyll in the mineral oil, more light is absorbed and transferred to the chlorophyll and the intensity of the emitted light for a given concentration of hCG can be increased.

In another embodiment of the present invention, liposomes (0.2 micron in diameter) are formed by high pressure extrusion of a suspension of x% phosphatidyl serine, y% phosphatidyl glycerol, z% phosphatidyl ethanolamine and q% phosphatidyl ethanolamine conjugated through an amide linkage with n-acetyl thyroxine in pH 7.4 buffer through a 0.2 micron pore membrane using a commercially available instrument designed for such purpose. Tripyrroledimethine dye (34) is dissolved in the lipophilic portion of the liposome. An enol ether, 1-[1-(10-carboxydecyloxy)-2-vinyl] pyrene (33) and the liposomes are covalently linked by a water soluble carbodiimide by means of a carboxamide linking group (Reagent 4).

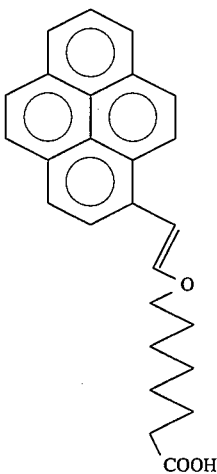

(33)

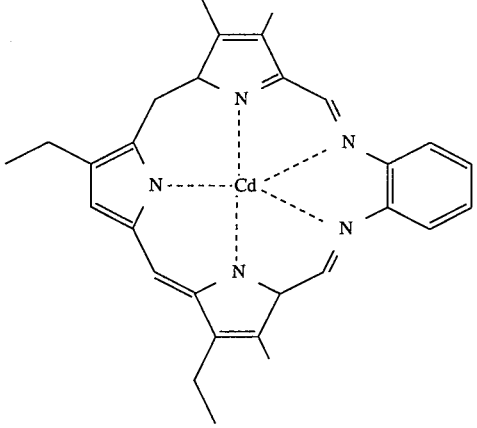

(34)

A monoclonal antibody for thyroxine is adsorbed onto the surface of a microtiter plate. Reagent 4 is combined in an aqueous buffered assay medium (500 mL) of pH 8.0 together with a serum sample suspected of containing thyroxine that contains anilinonaphthalene sulfonic acid to displace thyroxine from binding proteins (50 microliters). The assay medium is then combined with the microtiter plate and incubated at room temperature for 1 hour. The medium is separated from the plate, which is washed with buffer of pH 8 and then irradiated at 650 nm for a period of 1 minute and the resulting emitted light is measured by means of a luminometer. The value obtained is compared with values obtained by conducting a similar assay with known amounts of thyroxine. In this way the amount of thyroxine in the serum sample is quantitated.

In another embodiment the assay is for the determination of a particular blood group antigen on the surface of a red blood cell, namely, an A group antigen. Commercial latex particles having a surface comprising carboxyl groups and having a particle size of 150–500 nm are utilized. The latex particles are heated in ethylene glycol with the sensitizer, namely, chlorophyll, and the chemiluminescent compound 36, namely, the dioxene

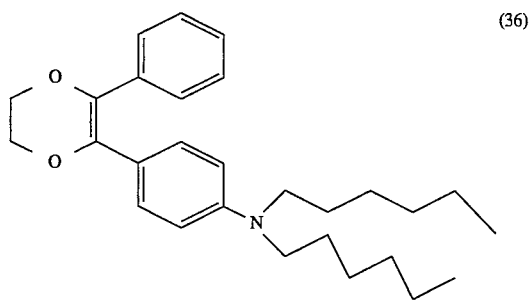

(36)

whereupon the two compounds are noncovalently dissolved in the particles. The particles are then covalently linked to an antibody for the A group antigen by treating a suspension of the particles with a water soluble carbodimide followed by addition of the antibody, incubation, separation of the particles by chromatography on a G100 size exclusion column and dilution of the particle containing fractions with Tris pH 8 buffer. This latex particle reagent is combined in the aqueous medium (500 ml) with whole blood (100 ml). The medium is incubated at 25° C. for a period of 10 minutes. Next, the cells are separated by brief centrifugation, washed with buffer and irradiated for a period of 30 seconds at >650 nm light with a tungsten source fitted with a 650 nm cutoff filter. The light emitted from the cells following the irradiation period is measured and compared to the amount of light obtained in samples known to be free of A group antigen red blood cells. Thus, the amount of light over a threshold level indicates the presence of the A blood group antigen.

In another embodiment the latex beads of the proceeding example are used together with latex beads that are identical except that Eu(TTA)$_3$ 35 is dissolved in the beads along with the photosensitizer and chemiluminescent compound and the antibodies bound to their surface are against the blood group B antigen.

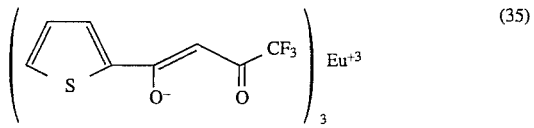

(35)

The Eμ(TTA)$_3$ is capable of increasing the rate of decay of luminescence of the activated CC and accepting the light energy and reemitting it at longer wavelength (615 nm instead of 380 nm). The assay is carried out as in the proceeding example. After irradiation the light emission from the cells is monitored. Emission at 380 nm is related to the presence of A antigen; emission at 615 nm is related to the presence of B antigen. Because of the different decay rates, the 615 nm emission can be monitored for the first 20 sec. and the 380 nm emission monitored after about one minute. The two intensities can be determined by resolution of the shape of the decay curve and/or by using filters designed to selectively transmit only one of the emission wavelength bands to a photodetector. The amount of each wavelength of light over a threshold level is related to the presence of the corresponding blood group antigen.

In an assay for a target polynucleotide sequence in a sample containing DNA, a 25-base oligonucleotide complementary with the target sequence is associated with CC 23 which is 9-phenylmethylidene xanthane. The CC and photosensitizer tetraoctadecylporphyrin are both dissolved into a latex particle as described above. The carboxyl groups on the latex surface are activated with carbodimide and N-hydroxy succinimide in ethylene glycol and then coupled to the oligonucleotide, on which is appended an amino group for purposes of binding to the particles. The latex particle reagent is mixed with the sample and a suspension of magnetic particles having bound to them a second 25 base oligonucleotide capable of binding to a different site on the target sequence. The medium is then heated to 75° C. and cooled to 55° C. to permit hybridization of the oligonucleotide to any target sequence present. The magnetic particles are then separated by means of a magnet. The pellet is then irradiated with 115 nm light from a He/Ne laser and the intensity of light emitted by the chemiluminescent compound 23 (about 350 nm)) following termination of the irradiation is measured. The light intensity is directly related to the presence of the target sequence.

In another embodiment of the present invention the particles of the invention are utilized as reference beads to provide calibration in an assay. One set of latex beads (180 nm) is dyed with chlorophyll. Another set of latex beads (180 nm), designated as "acceptor beads," is prepared containing the chemiluminescent acceptor, 1,2-diphenyl-3-p-dimethylaminophenyl-Δ$^{5,6}$-morpholine, which decays with a half life of 2 seconds. The chlorophyll dyed beads are coated with anti-fluorescein antibodies and the acceptor beads have avidin bound to their surface. A 50 μL serum sample suspected of containing human chorionic gonadotropin (hCG) is combined with a 200 μL solution containing an anti α-chain antibody labeled with fluorescein and an anti hCG β-chain antibody labeled with biotin. After incubating the mixture for 10 minutes, there is added to the mixture 200 μL of a suspension containing 2 μg of each of the above beads and 1 μg of 180 nm reference beads (particles in accordance with the present invention) containing both chlorophyll and 1-phenyl-2-p-dimethylaminophenyl-5,6-dihydro-1,4-dioxene, a chemiluminescent acceptor that decays with a 2 minute half life. The mixture is incubated for 10 minutes and then irradiated for one second with a tungsten-halogen lamp equipped with a 650 nm long pass cutoff filter. The light emitted ($S_T$) from the sample during the next 10 seconds is measured followed by measurement of the emitted light ($S_C$) over another 10 second interval. The light emitted during the second interval is entirely from the reference beads. The signal B, corrected for variables such as light intensity, phototube sensitivity, illumination time variations, temperature, etc., is then calculated from the expression: $B=S_T/CS_C-1$ where $C=S_T/S_C$ when no analyte is present. If desired, the one second irradiation and 10 second read sequence may be repeated several times prior to the final 10 second measurement of $S_C$. In this case $S_T$ is the sum of each of the readings except for the final reading and B is calculated in the same manner. B is then determined for one or more calibrators containing known amounts of hCG. Finally, the signal B is compared to the signal(s) B from the calibrator(s) to determine the concentration of hCG in the sample.

The present invention further encompasses compositions comprising a suspendible particle of 20 nanometer to 20 micron average diameter associated with a chemiluminescent compound and a photosensitizer. The chemiluminescent compound and the photosensitizer may be covalently bound to the particle matrix or may be noncovalently bound to or dissolved in the particle matrix. The particles will preferably be polymeric or be oil droplets or vesicles such as liposomes. Where the particle is a liposome, the chemiluminescent compound and photosensitizer may be associated with the lipid bilayer or dissolved in the aqueous interior of the liposome. For use in assays an spb member may be bound to the particles. Preferably, sbp bound particles will be 100 to 1000 nm in average diameter. Another aspect of the present invention relates to kits useful for conveniently performing an assay method of the invention for determining the presence or amount of an analyte in a sample suspected of containing the analyte. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. The kit comprises a composition comprising a suspendible particle having associated therewith a chemiluminescent compound and a photosensitizer, the particle having an sbp member bound to it. The photosensitizer can be associated with a particle, to which an sbp member is bound. The kit can further include other separately packaged reagents for conducting an assay such as an energy acceptor bound to an sbp member, additional sbp members, ancillary reagents, and so forth.

EXAMPLES

The invention is demonstrated further by the following illustrative examples. Parts and percentages recited herein are by weight unless otherwise specified. Temperatures are in degrees centigrade (° C.).

EXAMPLE 1

Preparation of Polystyrene Particles with Photosensitizer and Chemiluminescence Compound Incorporated Therein Particles used were 0.716μ carboxylate modified latex (CML) (Duke Scientific, lot #7638).

The Photosensitizer dye was tetra $nC_{10}$ phthalocyanine ($nC_{10}PC$) (Ultra Diagnostics, lot #GR11-82) 2.5 mg/ml in benzyl alcohol. M. W. 1180 (2.1 mM).

The chemiluminescence compound was p-(N,N-dioctadecylcarboxamidomethoxy) benzal-9-methylacridan ($C_{18}$ benzal acridan) 10 mM in benzyl alcohol, prepared as follows: To 10-dimethoxyphosphinyl-9-methyl acridan (Monatshi Chem. 114 3 (1988) (MW 303.27, 0.100 g, 3.3 mmol) in anhydrous tetrahydrofuran (THF) was added 0.413 mL of 1.6 M n-butyl lithium solution in hexane at −78° C. (acetone/dry ice bath) under argon. Upon the addition of the n-butyl lithium solution, the solution appeared yellow. A solution of the above amide in THF was added 20 minutes after the addition of n-butyl lithium. The reaction solution was permitted to warm to room temperature overnight.

The following day the product was isolated by TLC (Silica gel-3:7-ethylacetate/hexane). The isolated product was analyzed by mass spectrum analysis and NMR and stored in the dark.

Protocol for particle preparation: 0.8 ml ethylene glycol, 0.1 ml benzyl alcohol, 1, 2, 4, or 8 μl, respectively, of photosensitizer dye ($nC_{10}PC$) (particle preparations A, B, C, D, respectively) and 10 ul $C_{18}$ benzal acridan were mixed together and the mixture was heated to 100° to 110° C. for 1 min. Then, 0.1 ml of 0.716 μ CML was added to the mixture, which was heated for 5 min at 100° to 110°. The mixture was allowed to cool to room temperature. Equal volumes of ethanol were added and the mixture was centrifuged at 15K for 30 min. The centrifugate was decanted and the particles were combined with 2 ml of ethanol and centrifuged as described above. The wash and centrifugation steps were repeated using water. The particles were resuspended in water to a final volume of about 1 ml and 1.0% solids i.e., $4.95 \times 10^{10}$ particles per ml.

Light emitted by the particles was recorded using a Turner TD-20e Luminometer. The delay time was 0 and the integral was 20 seconds. Frequently, additional 20 second readings were taken to estimate decay half lives for the particles. Particles were illuminated for 60 seconds using a halogen lamp and 650 nm cutoff filter.

Typically, 10 ul of particle suspension from above was diluted to 1 ml in phosphate buffered saline (PBS); 100 ul of the diluted particles was used to determine relative light units (RLU) emitted. The results are summarized in the following Table 1:

TABLE 1

| Particles | RLU (20 second integrals) |
| --- | --- |
| A | 2611, 2104, 1778, 1552 |
| B | 3260, 2600, 2191, 1923, 1710 |
| C | 3725, 3032, 2587, 2272, 2034 |
| D | 3896, 3210, 2739, 2403, 2147 |

Effect of detergent: 10 μl of particles was diluted into 1 ml 1% triton X-100 (preparation F) instead of diluting with PBS as described above. The results are summarized in the following Table 2:

TABLE 2

| Particles | RLU (20 second integrals) |
| --- | --- |
| A | 2929, 2323, 1951, 1699, 1493 |

Very little detergent effect was observed. From this one might draw the conclusion that the photosensitizer and the CC have intercalated deep into the polystyrene particles.

EXAMPLE 2

Preparation of Polystyrene Particles with Photosensitizer, Chemiluminescent Compound and Energy Acceptor Incorporated Therein Run A. Reagents: (1) 1 ml 0.175μ CML (10% aqueous suspension), (2) Reaction Medium (1 ml ethoxyethanol containing 10 mM dioxene 10 wherein $X_2$ is $N(CH_3)_2$, 20 mM europium thenoyl trifluoroacetonate (EuTTA), 60 mM trioctylphosphine oxide (TOPO)) and (3) photosensitizer stock solution (tetra $nC_{10}$ phthalocyanine (see Example 1) ($nC_{10}Pc$) prepared as a separate solution in benzyl alcohol 2.5 mg/ml (m.w.=1180), approximately 2.1 mM).

One ml of CML particles was combined with 1 ml ethoxyethanol and warmed to about 100° in an oil bath. While stirring vigorously, 1 ml of Reaction Medium above was added to the particles. This was immediately followed by an aliquot of $nC_{10}PC$ (10, 25, or 50μ). Heating was continued for 10 min. An effort was made to keep the mixture just slightly below the boiling point of the water, but occasionally boiling was observed.

Run B. A procedure similar to A above was used to prepare particles in which chlorophyll a (chlor a) was the photosensitizer in place of $nC_{10}PC$ in the photosensitizer stock solution. The concentration of chlor a in the photosensitizer stock solution was 5 mM in benzyl alcohol. 10, 25, and 50μ aliquots of chlor a were used.

Following the 10 min heating period, the mixtures were removed from the oil bath and allowed to cool to room temp. The mixtures were then diluted with 6 ml ethanol and centrifuged at 15K for 30 min. The supernatants were discarded and the pellets resuspended by sonication in 50% ethanol solution. Centrifugation was repeated followed by another wash with 50% ethanol. The final pellet from centrifugation was resuspended in 10% ethanol solution to give a particle concentration of 1% by weight, i.e. 10 mg/ml ($3.35 \times 10^{12}$ particles per ml).

Chemiluminescence of the particles prepared above was studied. The particles (Run A or Run B) were diluted to 10 μg/ml in 0.1M Tris 0.3M NaCl, 25 mM EDTA, 1 mg/ml BSA pH 8.2. 0.1 ml of this diluted mixture was illuminated with a halogen lamp fitted with a 610 nm long pass filter for 60 sec. The first 20 sec integral of chemiluminescence was recorded on a Turner TD-20e luminometer. The results are summarized in Table 3.

TABLE 3

| | RLU |
| --- | --- |
| Run A ($nC_{10}PC$) | |
| 10 μl | 522 |
| 25 μl | 675 |
| 50 μl | 597 |

TABLE 3-continued

| | RLU |
|---|---|
| Run B (Chlorophyll a) | |
| 10 μl | 386 |
| 25 μl | 207 |
| 50 μl | 130 |

Detectability of the particles: 1 μg=$3.35 \times 10^8$ particles or $5.56 \times 10^{-16}$ mole. Defining detectability as 1 RLU, then $10^{-18}$ mole of the above particles (Run A) is detectable. This is slightly less than 1 million particles.

A particle (Run A) suspension at approximately 1 mg/ml was illuminated 30 sec with the halogen lamp and 610 nm filter. The particles were then placed in the fluorometer and the emission wavelength scanned. Some slight dioxane emission was observed at about 420 nm, but a major portion of the emitted light was from EuTTA at about 613 nm.

The same experiment was carried out with the particles from Run B and similar results were obtained.

EXAMPLE 3

Assay for Thyroid Stimulating Hormone (TSH)
Abbreviations:
$Ab_1$-biotin—biotinylated antibody for TSH
$Ab_2$-fluorescein ($Ab_2$-F)—monoclonal antibody for TSH, to which fluorescein is conjugated
$Ab_F$ or IgG($Ab_F$)—Antibody for fluorescein from cell line 3G1 prepared by standard hybrid cell technology as referred to above
BSA—Bovine serum albumin, Sigma Chemical Company, St. Louis, Mo., Cat. No. A-7888
D-$H_2O$—Deionized water
EDAC—1-Ethyl-3-(3-Dimethylaminopropyl) carbodiimide hydrochloride, Sigma Chemical Company
GB-Avidin—Glass beads (0.5 cm in diameter) coated with avidin; from Nichols Institute Diagnostics, San Juan Capistrano, Calif.
NaPi—Sodium phosphate
PBS—Phosphate buffered saline, 0.02 M NaPi, 0.15 M Na Cl pH7:3
RLU—Relative light units
SATA—S-acetylthioglycolic acid-NHS esters, from Sigma Chemical Company
sulfo-NHS—sulfo-N-hydroxysuccinimide, from Pierce Chemical company Preparation of Conjugate of Antibody for β TSH and Fluorescein ($Ab_2$-F)

A. Materials:
6-Carboxyfluorescein, (Kodak, Rochester, N.Y.); 4,9-dioxa-1,12-dodecane diamine, Aldrich Chemical Co., Milwaukee, Wis.); dry DMF distilled from calcium oxide; Ag-MP-1 (cr) anion exchange resin, BioRad Laboratories, Richmond, Calif.); monoclonal antibody for TSH ($Ab_2$) from hybrid cell line 9G3 prepared by standard hybrid cell culture technology using a method similar to that described by Kohler and Milstein, *Nature* (1975) 265:495–497.

B. Fluorescein Amine Hydrochloride (F-LC-Amine):
6-Carboxy fluorescein (10g, 26.6 mmole) was dissolved in dry dimethylformamide (DMF) (25 ml). N-hydroxysuccinimide (NHS) (Sigma Chemical Co.) (3.22 g, 28 mmole) was added as a solid to the DMF solution and allowed to dissolve. The mixture was then cooled in an ice bath. Dicyclohexylcarbodiimide (Aldrich Chemical Co.) (5.8g, 28 mmole) was dissolved in dry DMF (10 ml) and added all at once to the cold DMF solution. The mixture was stirred at ice bath temperature for 30 min. and then allowed to come to room temperature. The course of the reaction was followed by thin layer chromatography (TLC) (10% Methanol-$CH_2Cl_2$ containing 1% acetic acid). After 3 hours, formation of the fluorescein NHS ester was complete.

4,9-Dioxa-1,12-dodecane diamine (25.5g, 125 mmole) was diluted with dry DMF (10 ml). The fluorescein NHS ester reaction mixture was cooled in ice under an argon atmosphere and the diamine solution added dropwise over a period of 5 minutes. The cooling bath was removed and stirring was continued at room temperature. The course of the reaction was followed by tlc using the above system. When the reaction was judged complete, the mixture was diluted with water (100 ml) and cooled in ice to precipitate dicyclohexylurea, which was removed by filtration.

The filtrate was slurried with AG-MP-1(C1—) anion exchange resin and poured into a chromatography column. The resin was washed with 50% aqueous methanol until free diamine could no longer be detected by ninhydrin. The resin was then eluted with 0.1 N hydrochloric acid in 50% aqueous methanol. Fluorescein amine hydrochloride eluted first followed by 6-carboxy fluorescein. Pure fractions were pooled and taken to dryness on the rotary evaporator (rotovap). After drying under high vacuum 3.4 g of pure fluorescein amine hydrochloride was recovered.

C. Preparation of F-LC-Diglycolate (F-$LC_{18}$-COOH):
F-LC-amine (500 mg, 0.87 mmole), prepared as described in Part B above, was dissolved in 6 ml DMF. Triethylamine (TEA) (121μ, 0.87 mmole) was added to the DMF solution. Diglycolic anhydride (Aldrich Chemical Co.) (101 mg, 0.87 mmole) was dissolved in 1 ml DMF and added to the mixture. An additional 25 mg of diglycolic anhydride was added to force the reaction to completion as judged by silica gel TLC, methanol-dichloromethane acetic acid (20:79:1).

Solvent was removed on a rotovap and the residue was dissolved in methanol. The methanol solution was slurried with polystyrene Biobeads SM-2 (BioRad Laboratories). The beads were washed with water to remove diglycolic acid and TEA. The product was then stripped from the BioBeads in a large volume of methanol. After removal of methanol on a rotovap, 560 mg of product was recovered. This material was used without further purification or characterization.

D. Preparation of F-$LC_{19}$-NHS Ester:
F-$LC_{19}$-NHS ester was prepared by mixing 20 mg of F-$LC_{18}$-COOH (in 300μ of anhydrous DMF, prepared as described above in Part C) with 12 mg of dicyclohexylcarbodiimide (DCC) (in 100μ of anhydrous DMF). The reaction mixture was stirred gently at room temperature for 5 hours in a tightly closed vial. Then, the reaction mixture was filtered through glass wool to remove cyclohexylurea (side product of this reaction). The filtered reaction mixture was extracted with 2 ml of hexane (to remove unreacted DCC). The formation of F-$LC_{19}$-NHS was confirmed by TLC using a dichloromethane:methanol (80:20) solvent system.

E. $Ab_2$-F
$Ab_2$IgG was prepared by purification of $Ab_2$ by immobilized Protein A (Repligen, Inc., Cambridge, Mass.) according to standard procedures. $Ab_2$-F was prepared by reacting 1 ml 5.6 mg/ml $Ab_2$IgG in 0.05 M NaPi, 0.1 M NaCl/pH7.6 with 20μ of anhydrous DMF containing F-$LC_{19}$-NHS (IgG: F-$LC_{19}$-NHS≡1:20) at room temperature for 2 hrs. Then, the reaction mixture was purified by Sephadex G-25 (1.5×20 cm) column equilibrated in 0.02 M NaPi, 0.15 M NaCl, pH7.4. The hapten number was determined by standard procedures and was found to be 2.9 (2.9 fluorescein molecules per IgG). The final product was divided into aliquots and stored frozen.

Preparation of Biotinylated Antibody for TSH ($Ab_1$-Biotin):

Antibody for beta-TSH ($Ab_1$) was from hybrid cell line 2101 from BiosPacific, 405 Harlan St., Emeryville, Calif. Antibody for TSH ($Ab_1$, about 2–2.5 mg/mL in 0.05 M NaPi, 0.05 M NaCl/pH 7.8) and biotin-$LC_7$-NHS (Pierce Chemical Co., Rockford, Ill.) (first solubilized in DMF and a small aliquot used for the reaction) were mixed together and incubated for three hours at 4° C. In the reaction mixture, the molar ratio of the reactants was $Ab_1$:Biotin-$LC_7$-NHS=1:25. The uncoupled biotin was removed by Sephadex® G-25 column. The final conjugate was stored in 0.05 M NaPi, 0.001% Thimerosal/pH=7.4 at 4° C. or frozen.

Preparation of Anti-Fluorescein Antibody Coated Particles:

The particles used in this example were 0.04µ carboxylated polystyrene beads with singlet oxygen acceptor dye $C_{18}$ benzal acridan and singlet oxygen generator or sensitizer dye ($nC_{10}PC$) prepared as described in Example 1. EDAC/sulfo-NHS conjugation chemistry was used to couple the $Ab_F$ to these polystyrene beads ($Ab_F$-beads). Typically, 10 mL of 0.02 M NaPi containing 6 mg/mL of the carboxylated polystyrene beads from Example 1 and 11 mg/mL sulfo-NHS (pH adjusted to 5.5) were mixed with freshly prepared 1 mL of 200 mg/mL EDAC in $D-H_2O$. After incubating at room temperature (dark) for 25 minutes, the beads were centrifuged to remove excess EDAC (since EDAC causes microaggregation of these beads, it is possible to pellet them with conventional centrifuging by Sorval centrifuge using SA-600 rotor at 15000 rpm). The pelleted beads were resuspended in 3 mL of 0.005 M NaPi/5.8 by sonication and then transferred into the stirring protein solution containing 15 mL of 0.02 M Borax (Sigma Chemical Company), 0.08 M NaCl, 2 mg/mL 3G1 IgG($Ab_F$), and 8 mg/mL BSA/pH 8.9. The mixture was gently mixed (no stirring) overnight at 4° C. The remaining reactive groups on the beads (if any) were blocked by treating with 0.083 M glycine and 15 mg/mL BSA at pH 8.9 at 4° C. for 60 minutes. Uncoupled proteins were removed by successive washing with 0.05 M NaPi, 0.15 M NaCl at pH 7.6. The final pellet was resuspended in the washing buffer, sonicated and stored as is at 4° C. The final size of these beads was 140 nm.

TSH Assay:

TSH assay was performed by transferring 200 µL of TSH calibrators in TSH free serum (0, 0.1, 1, 10 and 100 ng/ml) into 12×75 nm glass test tubes, then followed by 100 µL of 2 µg/mL $Ab_1$-biotin and 1 µg/mL $Ab_2$-fluorescein (9G3) in assay buffer (0.05 M NaPi, 0.15 M NaCl, 4 mg/mL BSA/pH 7.6). This mixture was incubated at room temperature for 1 hour. To this mixture 100 µL of 1M $Na_3$ Citrate/pH 7.17 was added, followed by 100 µL of 1.0 mg/mL $Ab_F$-bead in assay buffer. The formed immune-complex was separated from the unbound fraction by 0.5 cm glass beads coated with avidin (one glass bead per tube used). The assay mixture was incubated with the glass beads for 2.5 hours at room temperature (shaking in dark). After incubation, each glass bead was washed with 4×1 mL PBS, 1% Triton X-100, 0.5 M NaCl/pH 7.2. Finally, each glass bead was illuminated for 1 minute and the emitted light was counted for 20 seconds using a luminometer from Turner Designs, model 20 e.

The results summarized in Table 4 show that TSH related specific signal was generated (sensitivity 0.1–0.5 ng/mL TSH in the calibrator).

TABLE 4

| TSH Assay | |
|---|---|
| TSH (ng/ml) | RLU |
| 0 | 350 |
| 0.1 | 550 |
| 1 | 800 |
| 10 | 1400 |
| 100 | 2200 |

Although the foregoing invention has been described in some detail by way of illustration and example for purposes of clarity and understanding, it will be obvious that certain changes or modifications may be practiced within the scope of the appended claims.

What is claimed is:

1. A method for calibrating light intensity emitted by a luminescent composition, said method comprising the steps of:

(a) combining in a medium a luminescent composition capable of emitting light upon irradiation and a composition comprising a solid matrix having incorporated therein a photosensitizer capable upon activation of generating singlet oxygen and a chemiluminescent compound capable of being activated by singlet oxygen, one of said compositions when activated by light having a decay time for light emission substantially greater than the decay time for the other, (b) irradiating said medium to activate said luminescent composition and said composition, (c) measuring the intensity of light emitted during the decay of the activated composition having the shorter decay time, (d) measuring the intensity of light emitted after said measuring of step (c) and after at least partial decay of the activated composition having the shorter decay time, and (e) comparing the intensity of the light emitted during the decay of the activated composition having the shorter decay time with the intensity of light emitted in step (d) to provide for internal calibration.

2. The method of claim 1 wherein steps b and c are repeated prior to step d.

3. The method of claim 1 wherein said activated composition comprising said solid material has the shorter decay time.

* * * * *